United States Patent [19]
Wyatt et al.

[11] Patent Number: 5,356,396
[45] Date of Patent: Oct. 18, 1994

[54] INFUSION APPARATUS

[75] Inventors: Philip Wyatt, Glendale; Gary Schaeffer, Valencia, both of Calif.; Freddy Zinger, Raanana, Israel

[73] Assignee: Medical Associates Network Inc., Glendale, Calif.

[21] Appl. No.: 954,528

[22] Filed: Sep. 29, 1992

[51] Int. Cl.⁵ .............................................. A61M 37/00
[52] U.S. Cl. ..................................... 604/283; 604/905
[58] Field of Search ................. 604/283, 905; 285/319

[56] References Cited

U.S. PATENT DOCUMENTS

| | | | |
|---|---|---|---|
| 4,511,359 | 4/1985 | Vaillancourt | 604/411 |
| 4,673,400 | 6/1987 | Martin | 604/283 |
| 4,752,292 | 6/1988 | Lopez | 604/244 |
| 4,834,716 | 5/1989 | Ogle, II | 604/192 |
| 4,946,445 | 8/1990 | Lynn | 604/192 |
| 4,964,855 | 10/1990 | Todd et al. | 604/283 |
| 4,998,713 | 3/1991 | Vaillancourt | 604/283 |
| 5,139,483 | 8/1992 | Ryan | 604/905 |
| 5,188,620 | 2/1993 | Jepson et al. | 604/283 |
| 5,199,947 | 4/1993 | Lopez et al. | 604/283 |

Primary Examiner—Jerome L. Kruter
Attorney, Agent, or Firm—J. E. Brunton

[57] ABSTRACT

A family of variously configured, new, improved and universally compatible infusion sites and medical connectors that employ a recessed cannula and which function to interconnect uniquely configured T sites, Y sites, heparin locks and the like with a liquid source, such as an I.V. source.

18 Claims, 13 Drawing Sheets

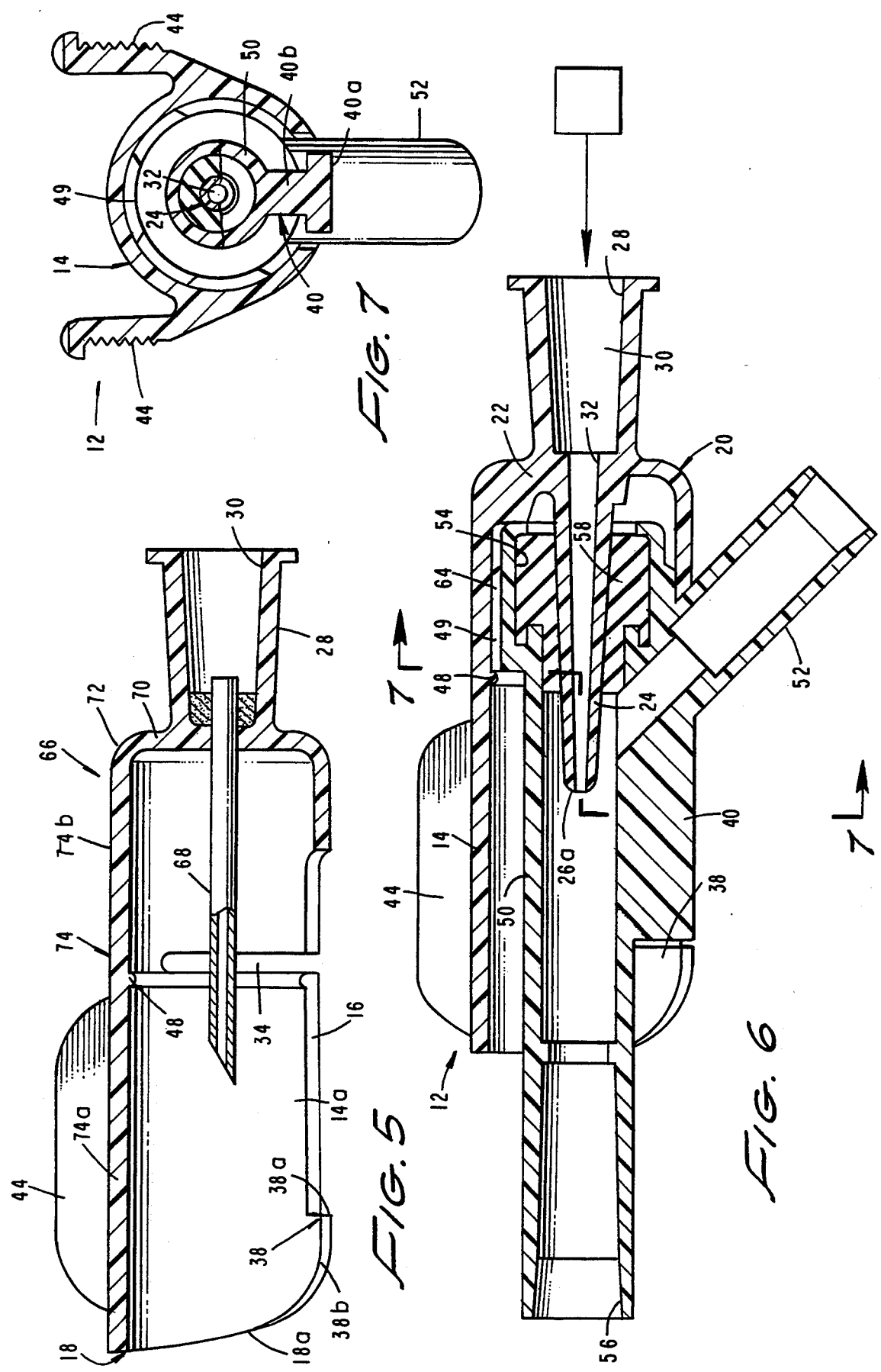

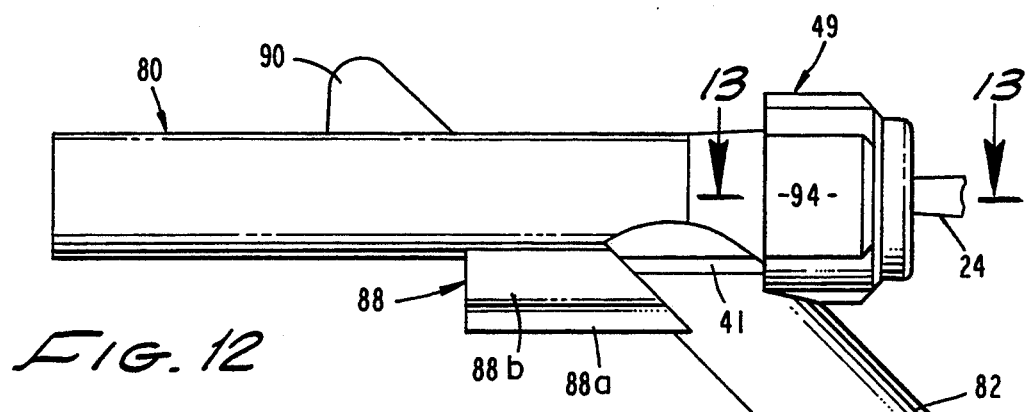
FIG. 12
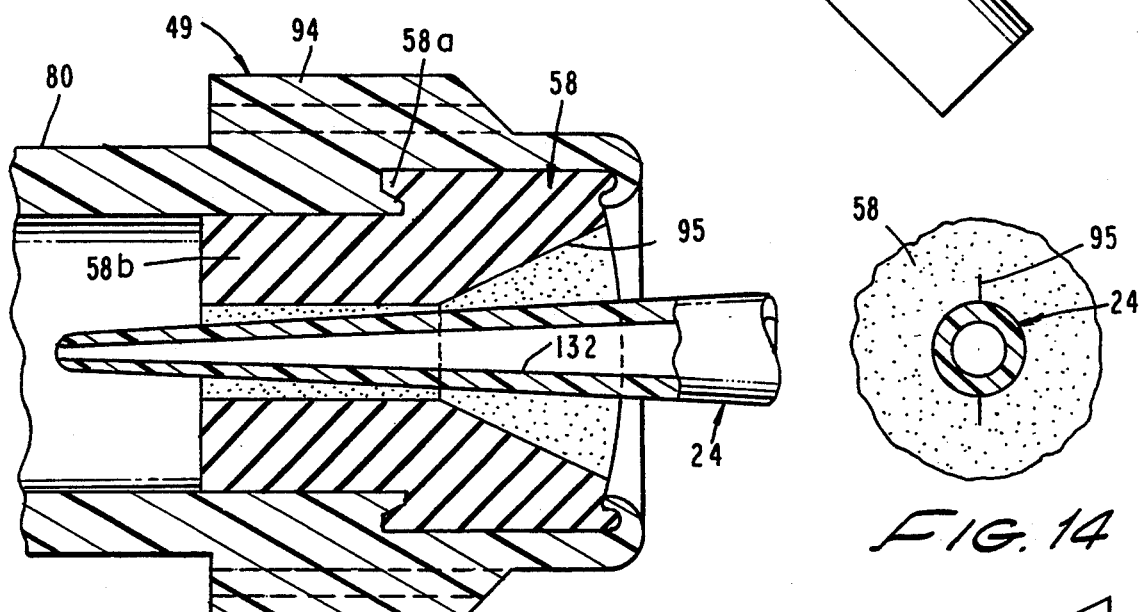
FIG. 13
FIG. 14
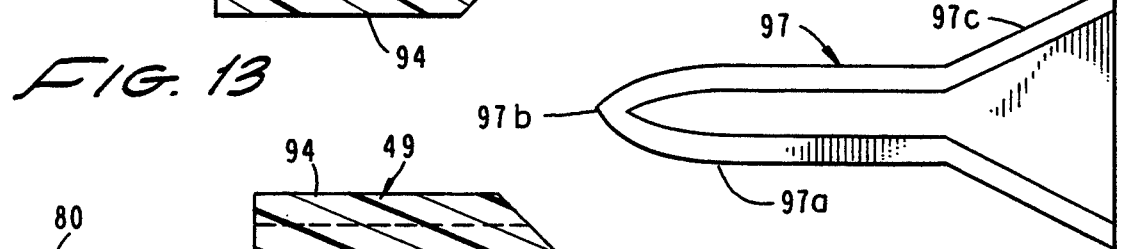
FIG. 15
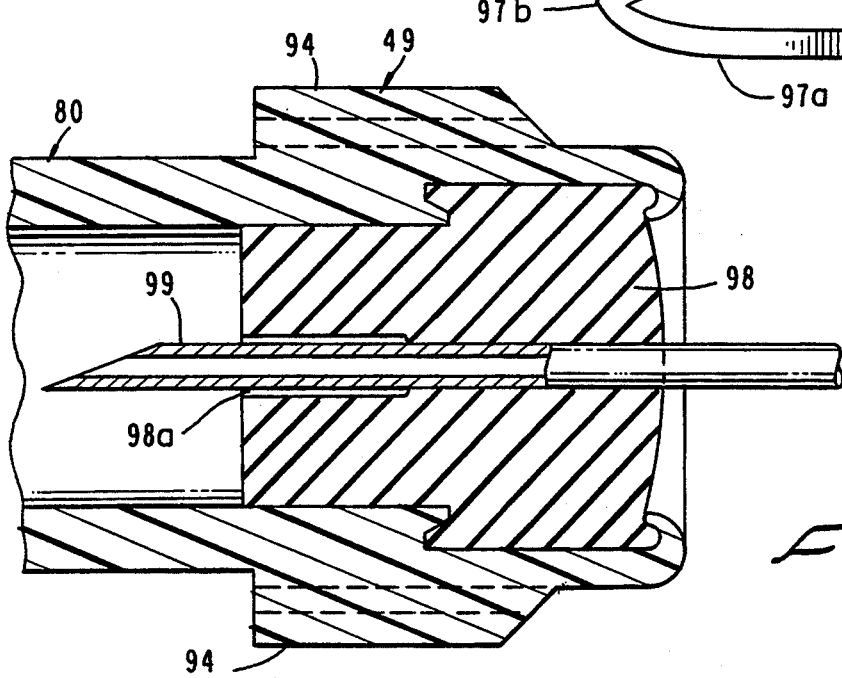
FIG. 16

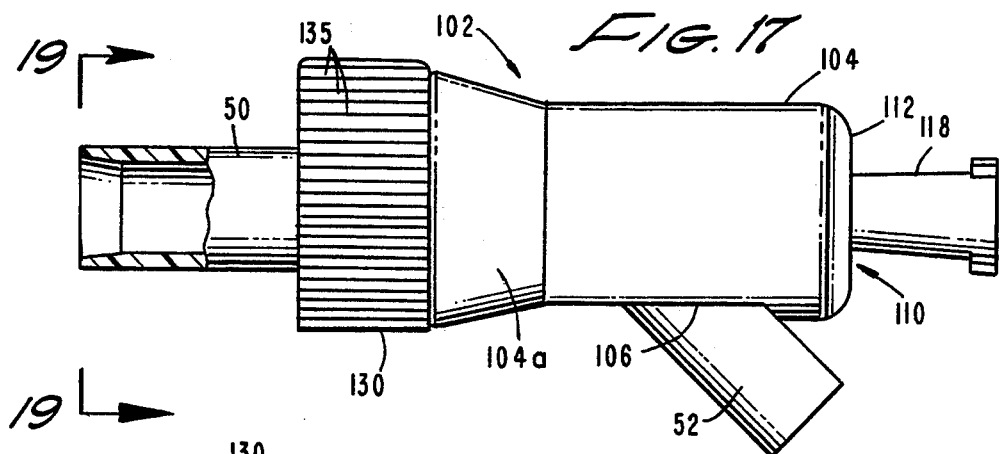
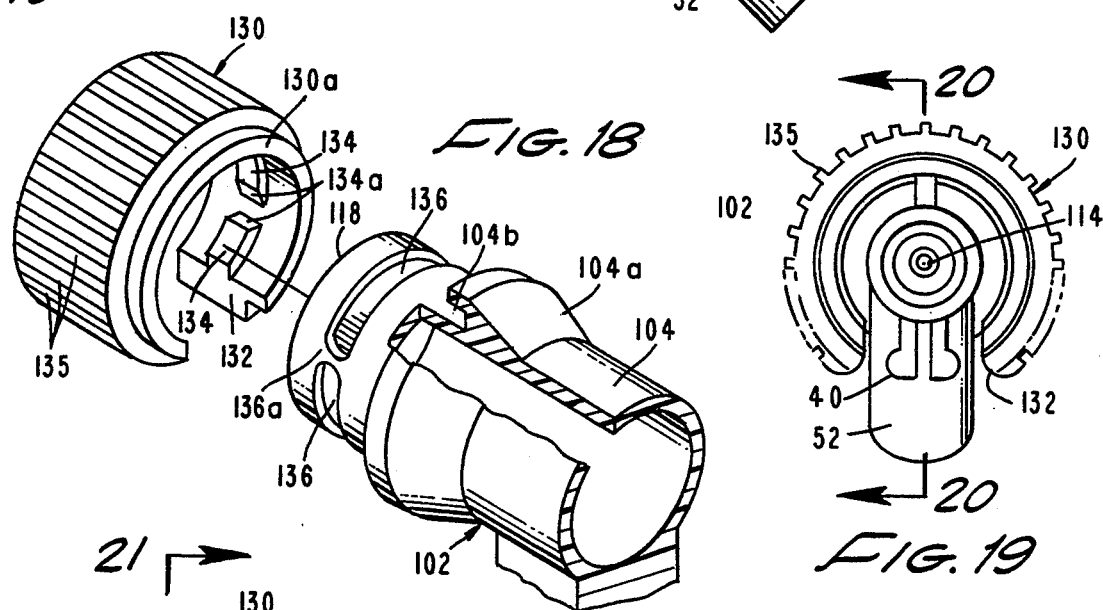
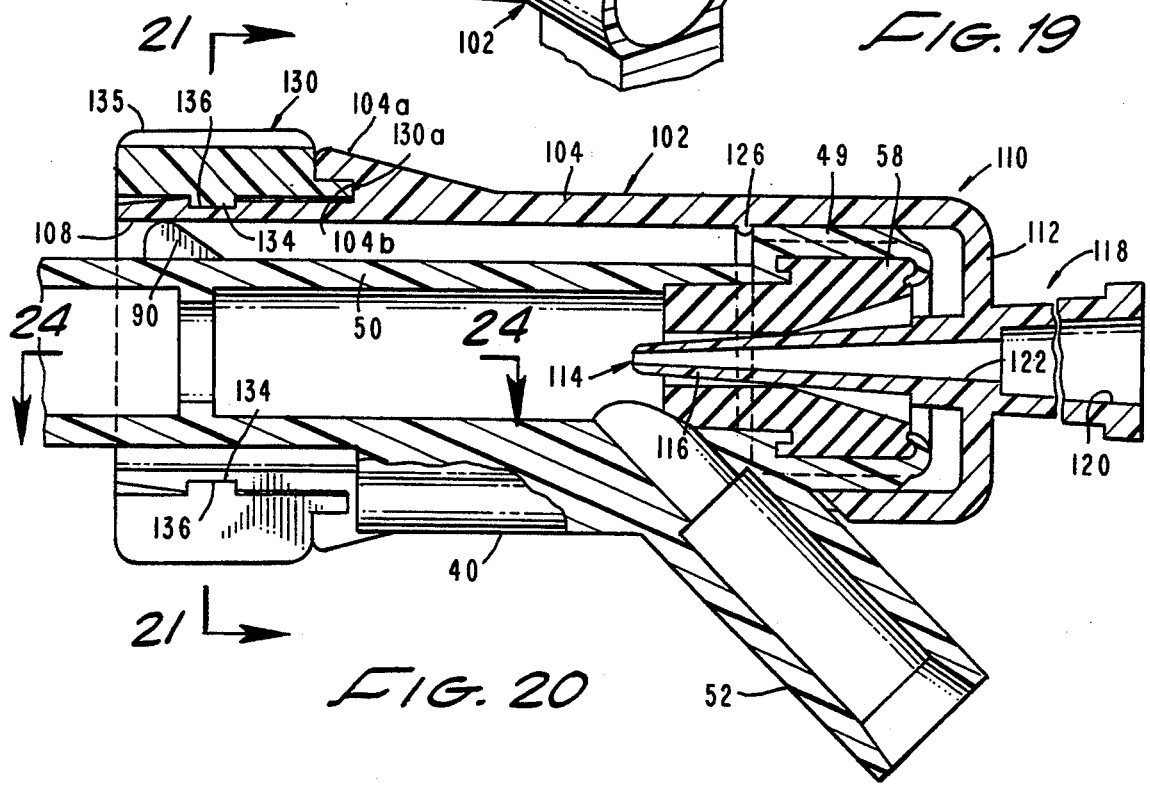

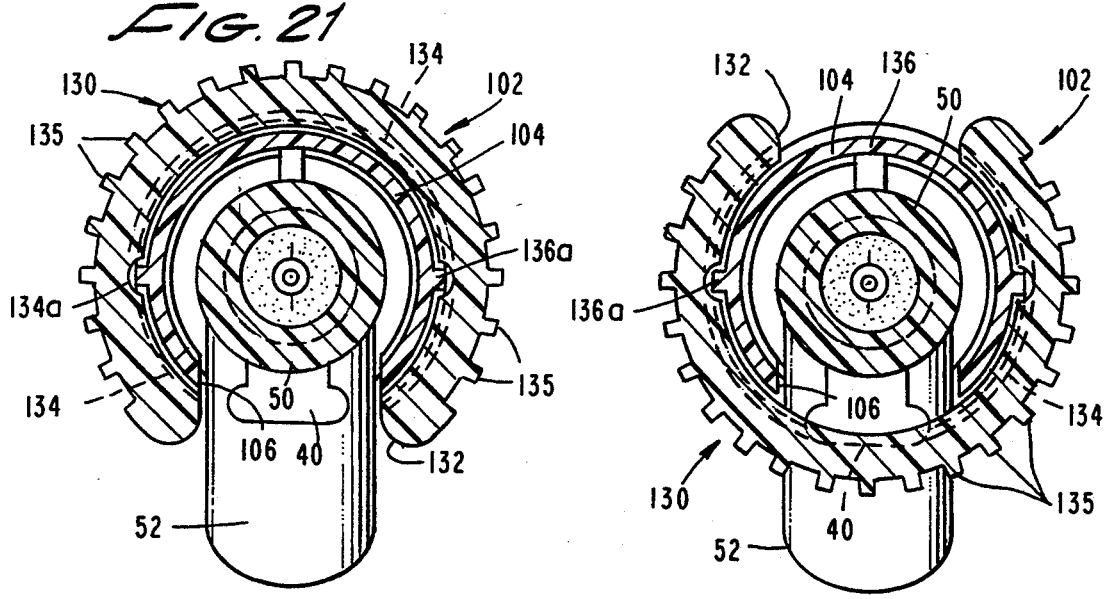
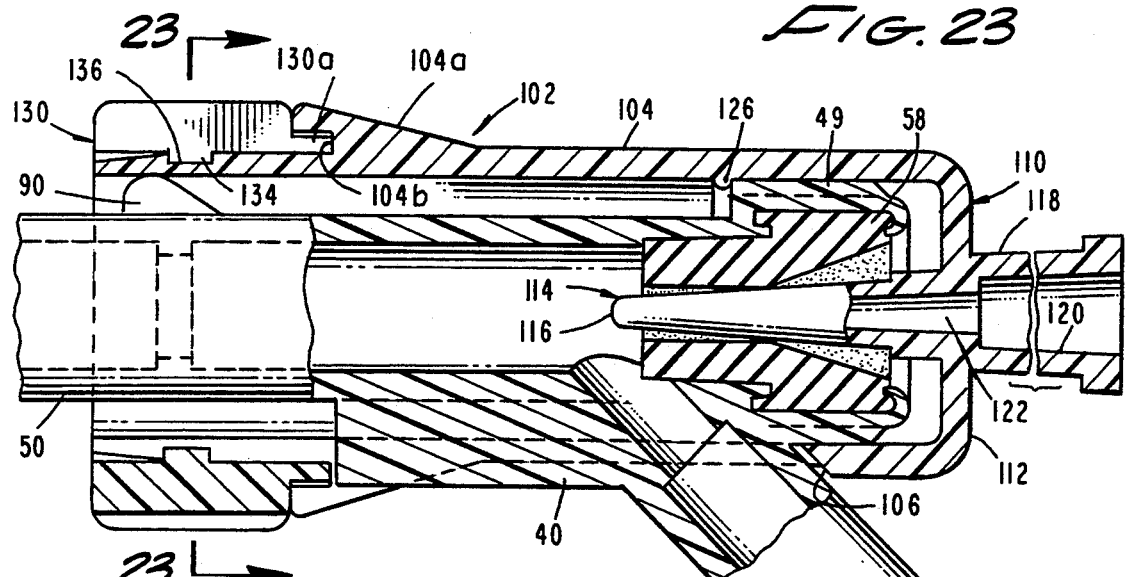
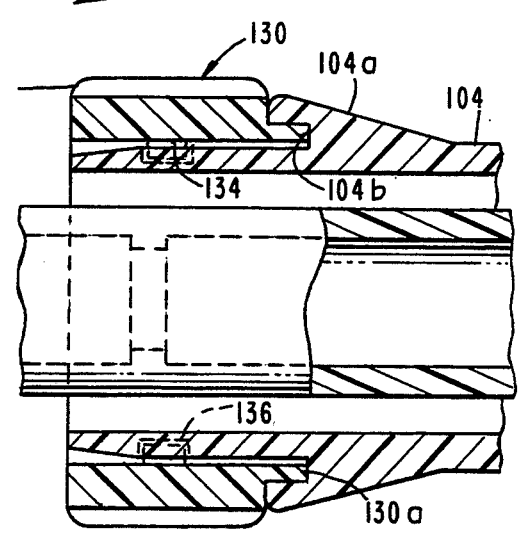

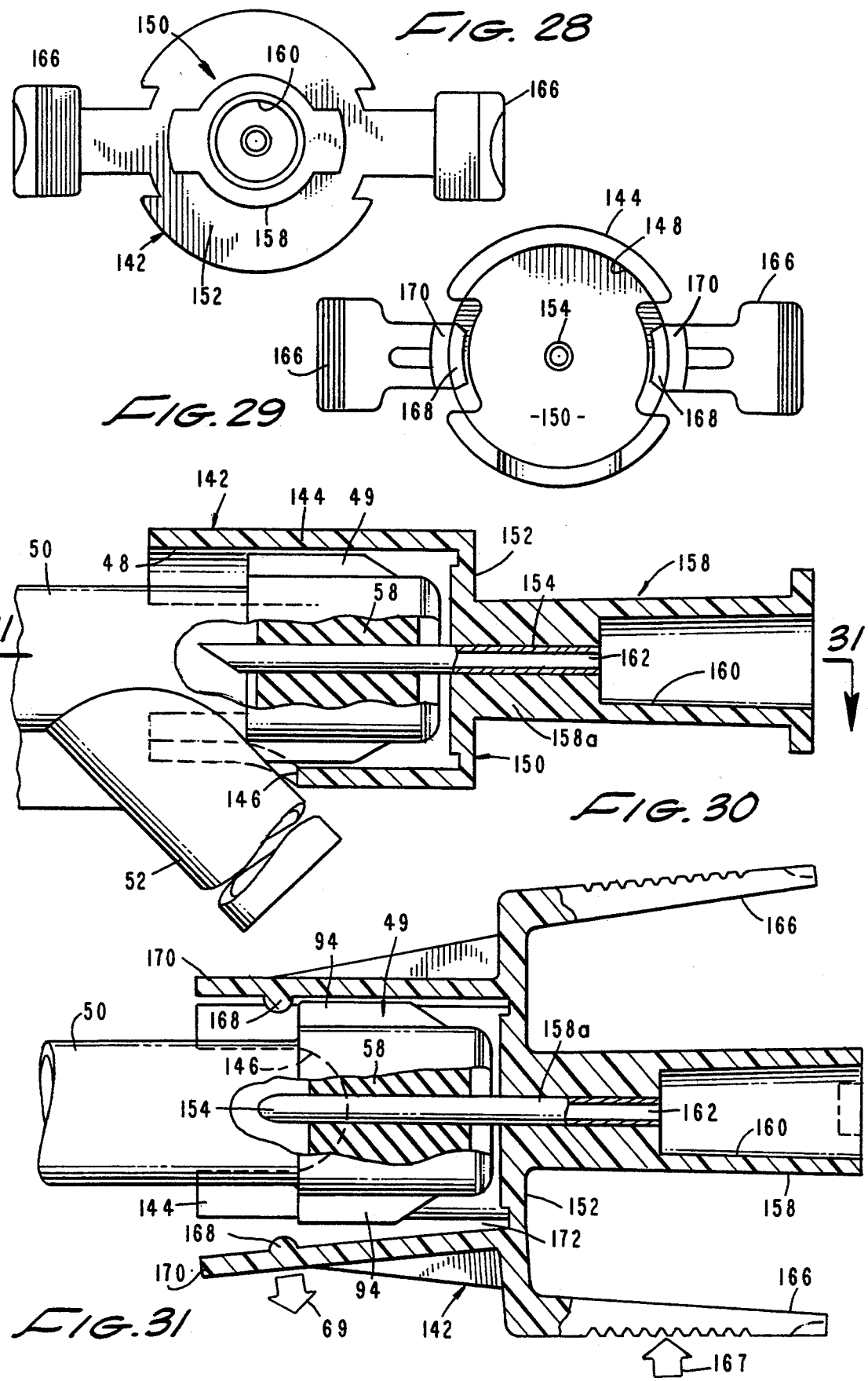

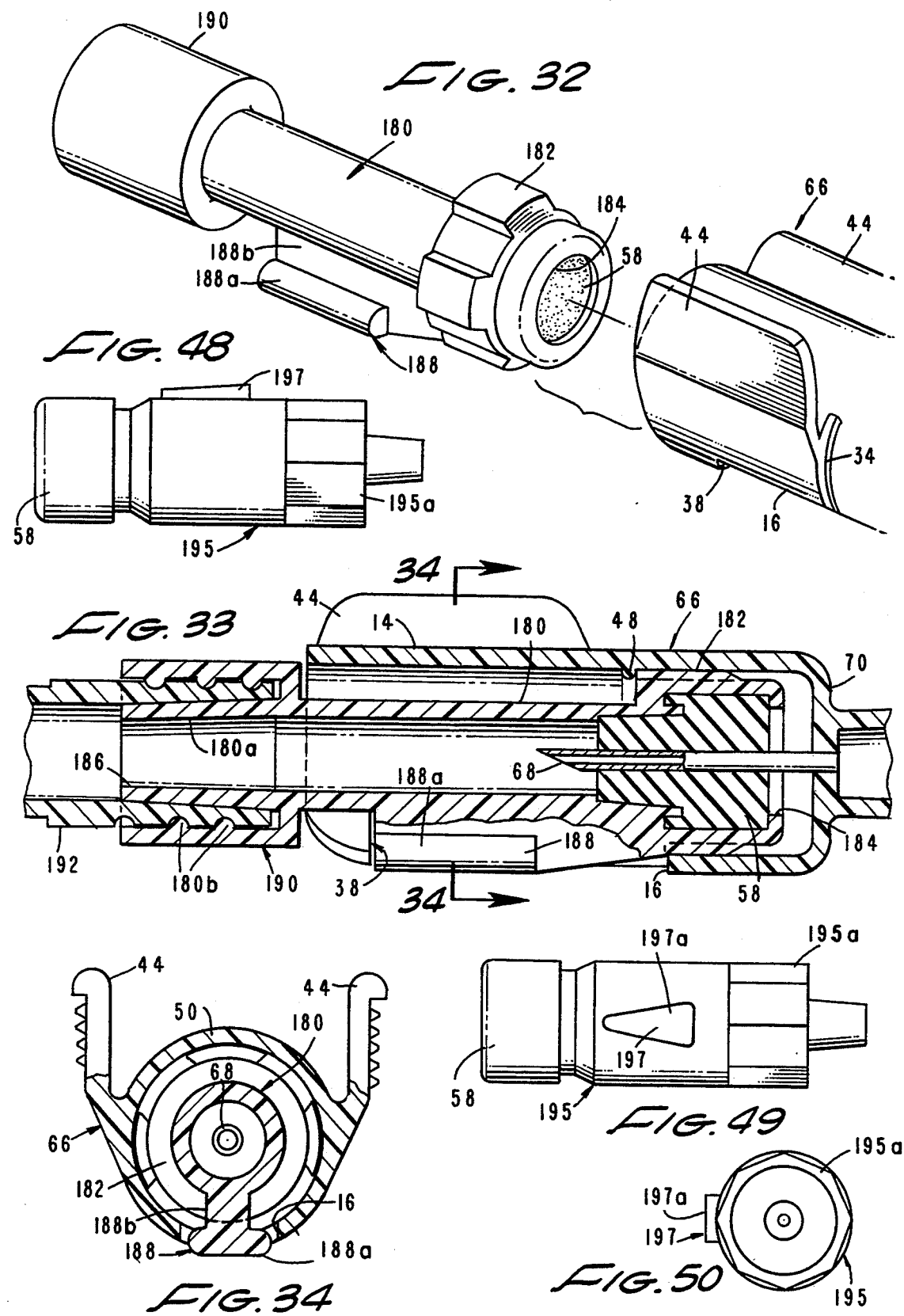

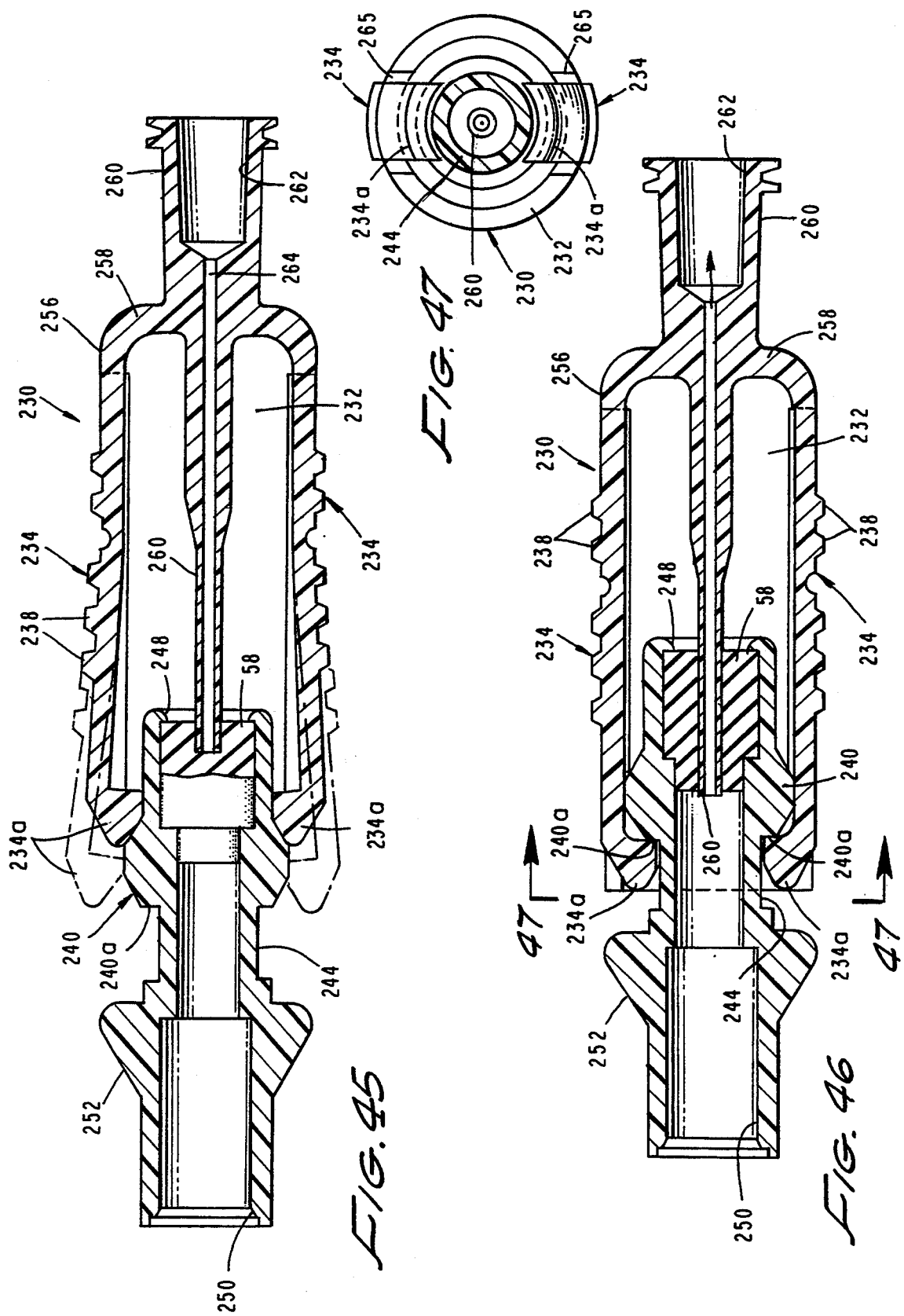

INFUSION APPARATUS

BACKGROUND OF THE INVENTION

FIELD OF THE INVENTION

The present invention relates generally to infusion systems, including medical connectors. More particularly, the invention concerns a family of new and improved entry port structures and cooperating medical connectors which employ a recessed needle. The medical connectors function to interconnect both standard and specially designed entry port structures such as T sites, Y sites heparin locks and the like with a liquid source, such as an I.V. source.

DISCUSSION OF THE INVENTION

The use of the intravenous or giving sets for the administration of parenteral fluids to a patient is a common practice. In its simplest form, the intravenous set comprises a length of tubing, one end of which is provided with a fitting for making a connection with a source of parenteral fluid such as a bottle or an elevated flexible bag. The other end of the tubing is typically provided with a needle which may be inserted into the vein of the patient. Frequently it is desirable to interconnect a secondary conduit with the length of tubing to enable infusion of a second parenteral fluid. This is generally accomplished through the use of an intermediate entry port structures, such as a "Y" site or "T" site unit. Both Y site and T site connector are units generally made with a straight tubular body portion and a hollow arm which extends laterally from the body portion. Typically at least one end of the body portion, as well as the open end of the arm portion, is provided with a seal of some type such as penetrable self-sealing septum adapted to accept a cannula such as the needle of a syringe or needle connector.

In use, the needle connector is mounted over the end of the Y or T site connector with the needle piercing through the self-sealing septum. In the past, substantial difficulties have been encountered in designing a needle connector which can be appropriately secured in place with respect to the Y or T site connector. In some instances, in order to ensure an appropriate connection, the needle connector has been designed to envelope the entire Y or T site connector. In other instances elaborate multi-part connectors have been designed to positively lock the needle connector to the Y or T site connector. Exemplary of this latter class of devices are those described in U.S. Pat. No. 4,998,713 issued to Vaillancourt. Many of the prior art devices, including the Vaillancourt devices, also include a protective shield of some type within which the needle is mounted. Another connector, which also provides a protected cannula, is disclosed in U.S. Pat. No. 4,834,716 issued to Ogle, II. Still another type of prior art connector is described in U.S. Pat. No. 4,964,855 issued to Todd, et al. A connector shown in U.S. Pat. No. 4,752,292 issued to Lopez, et al. discloses various types of locking mechanisms for use with non-standard, specially configured Y sites and other specially configured sealed port structures.

A principal drawback of many of the prior art connector devices is the fact that frequently the devices cannot be used with Y sites, T sites and heparin locks of standard construction. Further many of the prior art connectors cannot be securely attached even to Y or T sites of specially non-standard construction, and therefore can become relatively easily separated therefrom. If the connector separates from the entry port structure, the flow of parenteral liquids to the patient will, of course, interrupted. The result can be catastrophic, particularly if the patient is in intensive care. To avoid such separation, tape is sometimes used in an to attempt to more securely interconnect the needle connector with the standard or specially configured Y or T site. However, this approach is quite cumbersome, inconvenient and generally undesirable since the tape can also easily work loose thereby permitting the needle connector to separate from the Y or T site.

To avoid undesirable separation of the needle connector from the Y site, T site, or other entry port structure several complex, multi-port connector devices have been suggested. Typically, these devices are often difficult to use and are quite expensive to manufacture. Additionally, many of the devices do not have universal applicability and are usable only with particular types of Y or T sites thereby further limiting their practicability.

The thrust of the present invention is to overcome the drawbacks of the prior art by providing an easy to use, elegantly simple family of infusion devices, including low dead space infusion sites and universal connectors which provide a positive and secure connection to all commonly used Y sites, T sites and heparin locks. The devices are user friendly, highly reliable and can be inexpensively manufactured. They will accept commercially available Y sites and T sites of varying sizes and configurations and advantageously provide both tactile and audio locking features. Further, the devices provide uniquely configured needle shrouds which effectively protect against needle stick.

SUMMARY OF THE INVENTION

It is an object of the present invention to provide a family of low dead space entry port structures, such as heparin locks and Y and T sites, which can be aseptically interconnected with a source of fluids, such as an I.V. source, using connectors, or couplers of unique design. The connectors uniquely mate with the entry port structures in a manner which positively prevents accidental separation of the connectors from the entry port structure. In this way, the accidental interruption of the flow of parenteral liquids to the patient is effectively prevented.

Another object of the invention is to provide an infusion system in which the connectors can be mated with a number of different types of commercially available, entry port structures of both standard and special construction and include extended length shrouds which function to positively prevent accidental needle stick. The connectors will accept large and small diameter Y and T sites as well as heparin locks and will accommodate Y sites having both high and low Y locations.

Another object of the invention is to provide an infusion system of the aforementioned character in which the connectors embody both tactile and audio locking features to ensure positive interconnection with the mating infusion site. The locking elements are advantageously disposed within a cylindrical boundary generally defined by the boundary of the shroud portion of the connector and extensions thereof.

Another object of the invention is to provide an infusion system as described in the preceding paragraphs in which the connector's positively resist disengagement and embody dual locking mechanisms to guard against accidental separation. Further, the connectors include specially configured mounting surfaces to enable easy interconnection of the device with the patient.

Still another object of the invention is to provide connectors of the character described having easy-to-use and release locking mechanisms including textured release arms, grips, rotating locking collars and pen snaps.

Another object of the invention is to provide connectors of the type described in the preceding paragraphs which effectively eliminate wobbling and pistoning (and the possible contamination resulting therefrom) of the needle within the septum and which can embody both metal and plastic cannulas.

Yet another object of the invention is to provide an infusion system which includes entry port structures embodying septums of unique design that will sealably accommodate cannulas of various types and will permit repeated puncture without leaking.

Another object of the invention is to provide a family of mating infusion components of the character described which are safe and easy to use, are constructed of yieldably deformable, clear plastic materials that are compatible with most drugs and parenteral liquids and are inexpensive to manufacture in large volume.

BRIEF DESCRIPTION OF THE DRAWINGS

FIG. 5 is a cross-sectional view similar to FIG. 2 but showing an alternate form of medical connector of the invention which embodies a metal needle rather than a blunt plastic cannula.

FIG. 6 is a side, cross-sectional view of the connector of FIGS. 1 and 2 interconnected with a low dead space Y site unit which forms a novel component of the apparatus of the present invention.

FIG. 7 is a cross-sectional view taken along lines 7—7 of FIG. 6.

FIG. 12 is a side elevational view of the Y site construction.

FIG. 13 is an enlarged, fragmentary, cross-sectional view taken along lines 13—13 of FIG. 12.

FIG. 14 is a fragmentary end view of the slit septum portion of the Y site heparin lock unit.

FIG. 15 is a side elevational view of a cutting tool of the character used to cut the uniquely shaped slit in the septum.

FIG. 16 is an enlarged, fragmentary, cross-sectional view of an alternate form of septum of the Y site unit.

FIG. 17 is a side elevational view of yet another embodiment of the connector of the apparatus of the invention shown in position around a Y site unit.

FIG. 18 is a fragmentary, perspective view partly in section illustrating the construction of the connector of this latest form of the invention.

FIG. 19 is a view taken along lines 19—19 of FIG. 17.

FIG. 20 is an enlarged cross-sectional view taken along lines 20—20 of FIG. 19.

FIG. 21 is a cross-sectional view taken along lines 21—21 of FIG. 20.

FIG. 22 is a side elevational, cross-sectional view similar to FIG. 20 but showing the connector of this form of the apparatus in a locked position.

FIG. 23 is a cross-sectional view taken along lines 23-23 of FIG. 22.

FIG. 24 is a fragmentary, cross-sectional view taken along lines 24—24 of FIG. 20.

FIG. 28 is a view taken along lines 28—28 of FIG. 26.

FIG. 29 is a view taken along lines 29—29 of FIG. 26.

FIG. 30 is a cross-sectional view taken along lines 30—30 of FIG. 27.

FIG. 31 is a cross-sectional view taken along lines 31—31 of FIG. 30.

FIG. 32 is a generally perspective view of a heparin type lock of the apparatus of the present invention and a fragmentary portion of a connector unit for interconnection with the heparin lock.

FIG. 33 is a cross-sectional view illustrating the heparin lock of FIG. 32 interconnected with a connector unit of the character shown in FIG. 5.

FIG. 34 is a cross-sectional view taken along lines 34-34 of FIG. 33.

FIG. 45 is a cross-sectional view taken along lines 45—45 of FIG. 43.

FIG. 46 is a cross-sectional view taken along lines 46—46 of FIG. 44.

FIG. 47 is a cross-sectional view taken along lines 47—47 of FIG. 46.

FIG. 48 is a side elevational view of another form of heparin lock of the present invention.

FIG. 49 is a top view of the alternate form of heparin lock.

FIG. 50 is an end view of the heparin lock of FIGS. 48 and 49.

DESCRIPTION OF THE INVENTION

Figure 1:
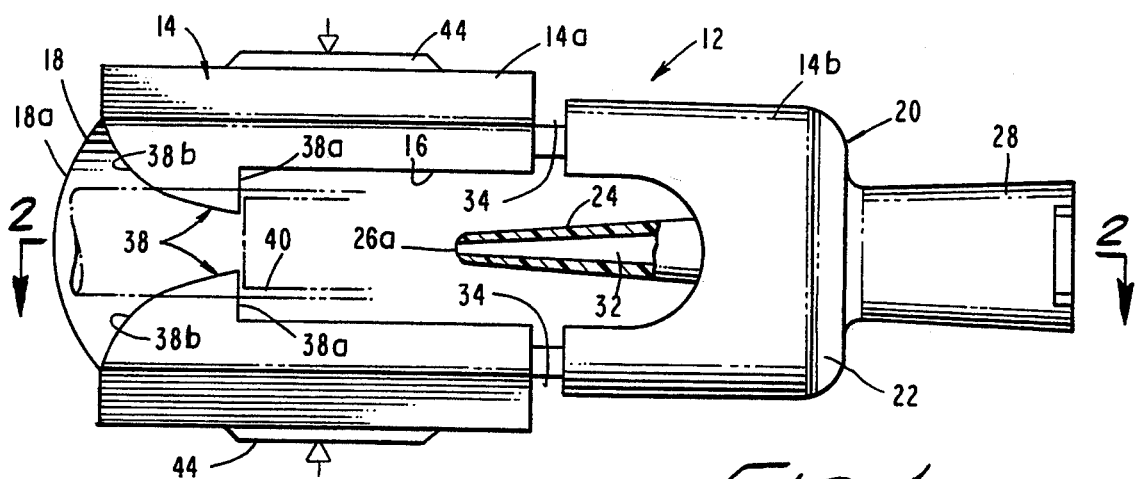
FIG. 1 is a top plan view partly in section of one form of the medical connector of the apparatus of the invention.
Figure 2:
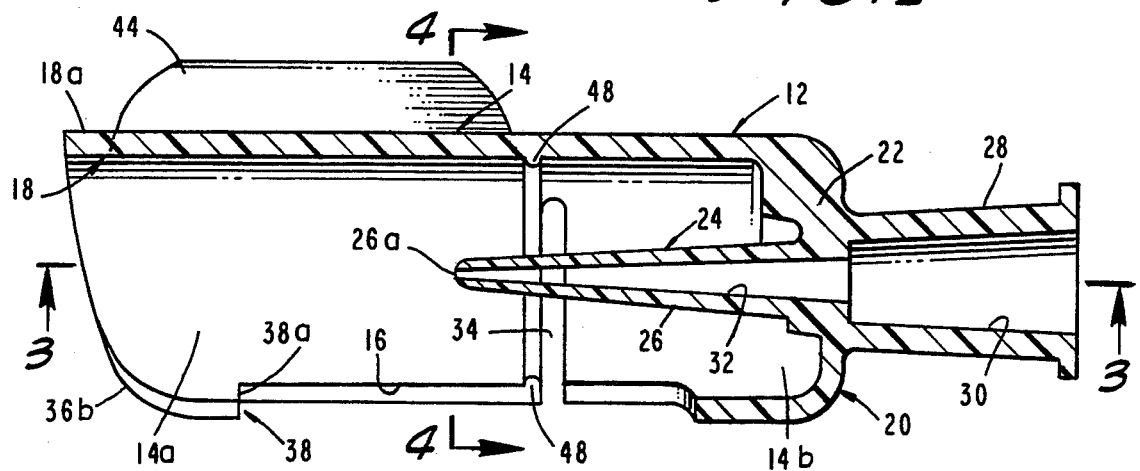
FIG. 2 is a cross-sectional view taken along lines 2—2 of FIG. 1.

Referring to the drawings and particularly to FIGS. 1 and 2, one form of medical connector of the apparatus of the invention is there shown and generally designated by the numeral 12. The connector of this form of the invention is adapted for use with a variety of different types of entry port structures, including Y sites of the character having a cylindrical body portion and an arm portion extending laterally therefrom. The connector here comprises a sheath assembly including a generally cylindrical sheath portion defined by an elongated cylindrical wall 14 having an elongated slot 16 for receiving the arm portion of the Y site unit. Cylindrical wall 14 includes an open first end 18 defined by an upper curved wall 18a (FIG. 1) and a second end 20 which, as best seen in FIG. 2, is closed by an end wall 22. End wall 22 functions as a cannula support for supporting either a metal or plastic cannula.

The cannula shown in FIGS. 1 and 2 comprises a plastic cannula 24 which is connected to cannula support wall 22 and extends inwardly a substantial distance into the interior of sheath portion 14 in the manner best seen in FIG. 2. Cannula 24 comprises a tapered wall 26 one end of which interconnects with cannula support wall 22 in the manner shown in FIG. 2. The opposite end of wall 26 terminates in a septum penetrating extremity 26a which includes rounded tip portion adapted to readily penetrate a slitted septum of the character presently to be described. Cannula 26 may be integrally formed with support wall 22 or, in some instances, may comprise a separate element which is either fixedly or removably interconnected with wall 22.

Extending rearwardly of wall 22 is a connecting portion 28 having a fluid passageway 30 which communicates with a fluid passageway 32 defined by cannula wall 26. Portion 28 can be suitably interconnected with a source of liquid such a parenteral fluid 60 by means of a luer connector, a length of plastic tubing 62 (FIG. 6) or in a manner well known to those skilled in the art. As best seen in FIG. 1, cylindrical wall 14 comprises first and second wall portions 14a and 14b which are divided by a circumferentially extending slot 34 the purpose of which will presently be described.

Forming an important aspect of the connector of the present form of the invention is locking means for releasably locking the Y site in position within the connector. These locking means here comprise a pair of spaced-apart, oppositely disposed barb-like locking segments 38 which are located proximate open end 18 of wall 14. As indicated in FIG. 1, the transversely extending inboard edges 38a of the locking segments are adapted to lockably engage an upstanding locking protuberance 40 provided on the Y site which is shown in FIG. 1 by dotted lines (see also FIG. 7). Forwardly of locking segments 38 are inwardly sweeping curved surfaces 38b which guide entrance of protuberance 40 of the Y site into slot 16 after the protuberance passes by edges 38a. The cylindrical wall 14 of the sheath assembly is constructed of a relatively thin plastic material which is yieldably deformable so that as protuberance 40 is urged between curved surfaces 38b, the locking segments 38 will spread apart a sufficient distance to permit protuberance 40 to pass by and to snap into a locked position within slot 16. The wall of the Y site arm is provided with grooves 41 to guide passage of wall 14. Once the protuberance 40 passes elements 38, they will return to their at-rest position and will be locked against removal by edges 38a. It is important to note that the sheath assembly, including the locking means, is substantially disposed within a cylindrically shaped boundary which roughly corresponds to the cylindrical boundary of cylindrical wall 14 and extensions thereto.

Figure 4:
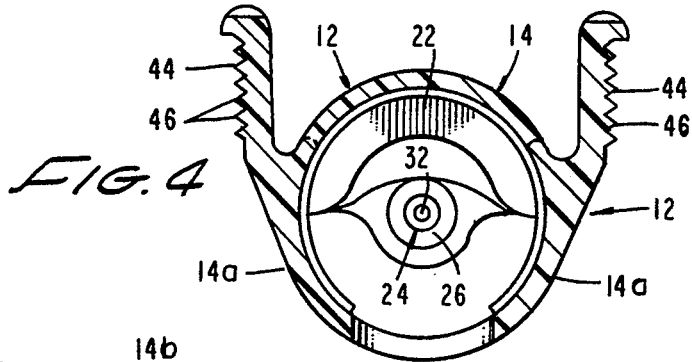
FIG. 4 is a cross-sectional view taken along lines 4—4 of FIG. 2.
Figure 3:
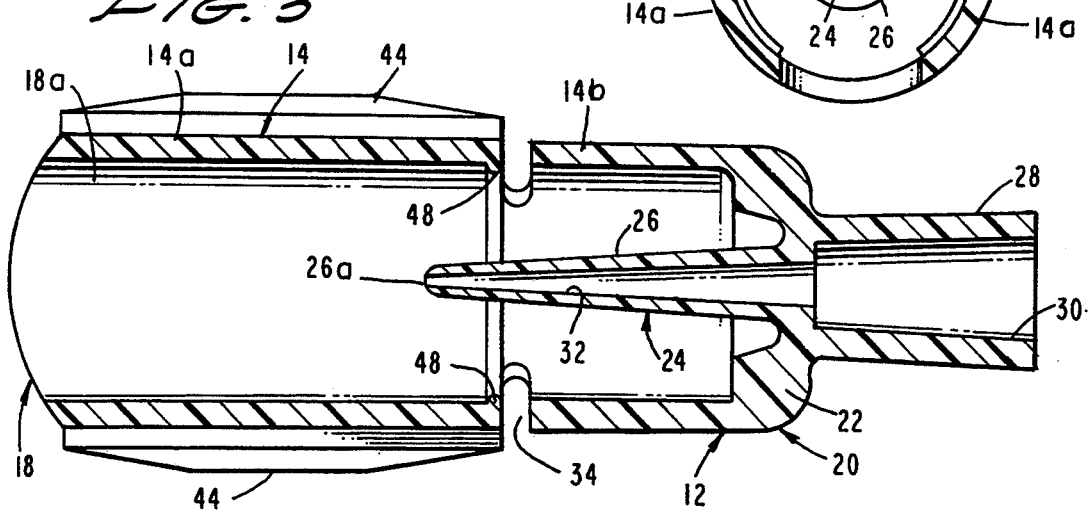
FIG. 3 is a cross-sectional view taken along lines 3—3 of FIG. 2.

The apparatus of this form of the invention also includes release means for moving the locking means from a locked position to an unlocked position. The release means here functions to spread apart barb-like segments 38 a sufficient distance to permit withdrawal of protuberance 40 of the Y site from slot 16. More specifically, the release here means comprises a pair of spaced-apart, wing-like gripping members 44 which, as best seen in FIG. 4, extend tangentially from first wall portion 14a of cylindrical wall 14. Gripping members 44 are provided with rounded, non-snag corners, and with gripping striations 46 which provide a textured surface to facilitate gripping the members in a manner to urge them toward one another. Due to the resilient character of the plastic as the gripping members are urged toward one another, elements 38 will move from the first at-rest or locked position to a second unlocked or open position wherein the space between the elements is sufficient to permit passage of protuberance 40 of the Y site unit. With the gripping members urged toward one another, the protuberance 40 on the Y site will clear locking edges 38 permitting smooth and easy disconnection of the Y site unit from the connector 12. The configuration of the wing-like gripping members is such that they provide a flat patient-engaging surface or base to permit the device to be positively and securely taped to the patient in a stable manner.

Figure 8:
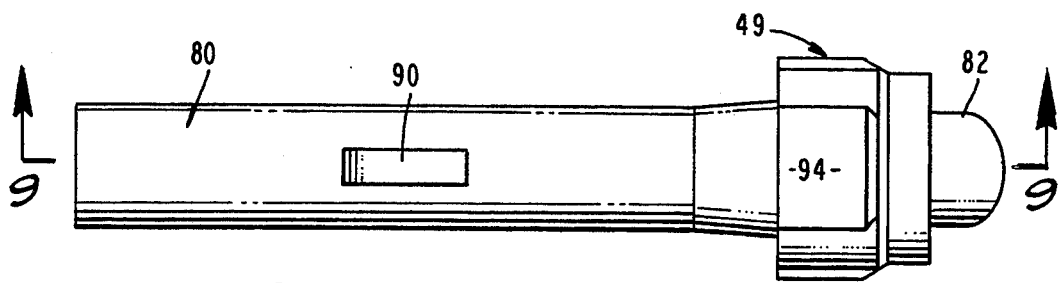
FIG. 8 is a top view of a low dead space Y site unit of the present invention.

In the form of the invention shown in the drawings, second locking means are also provided for releasably locking the connector to the Y site. This second locking means is here provided in the form of a pen snap type lock which comprises a circumferentially extending bead 48 located on the inner circumference of cylindrical wall 14. As the head portion of the Y site enters the connector it will frictionally engage bead 48. However, upon the continued exertion of an inward force on the Y site the head portion 49 (see also FIGS. 8 and 9) will slip by bead 48 and protuberance 40 of the Y site will move into locking engagement with the first locking means, namely elements 38.

Connector 12 is preferably constructed from a durable, springy clear plastic material that can be injection molded and one that is fully compatible with commonly used drugs and parenteral fluids.

Turning now to FIGS. 6 and 7, the medical connector 14 of the character described in the preceding paragraphs is shown interconnected with a low dead space Y site unit of the present invention. As best seen in FIG. 6, the low dead space Y site unit there shown comprises a tubular body portion 50 and an arm portion 52 which extends laterally therefrom. The Y site also includes first and second end portions defining ports 54 and 56, the first port 54 being closed by a uniquely constructed penetrable seal 58, the nature of which will presently be described. An important feature of the Y site of this form of the invention, is the previously identified locking protuberance 40 which functions to lockably engage barb-like segments 38 provided on sheath 14 of the connector unit. The configuration of protuberance 40 is best seen by referring to FIGS. 6 and 7 where it is to be noted that the protuberance includes an upper plate-like portion 40a which is connected to a body portion 40b which, in turn, is interconnected with tubular body portion 50.

In using the apparatus of the invention, the medical connector 14 is interconnected with a suitable source of liquid to be infused in the patient such as a parenteral liquid contained within a suitable source 60 (FIG. 6) such as a bottle or elevated flexible bag. The source of liquid can be interconnected with the medical connector 14 by means of a length of plastic tubing 62 which is suitably interconnected with connecting portion 28 of the connector. The Y site unit is then inserted into the open mouth 18 of shroud portion 14 and urged inwardly with sufficient force to cause cannula 24 to penetrate septum 58. As the Y site is introduced into the connector unit, protuberance 40 of the Y site will ride along curved surfaces 38b of the shroud urging them to separate. Because the shroud is provided with the previously identified, strategically located, circumferentially extending slot 34, the locking elements 38 will be permitted to resiliently deform outwardly a sufficient distance to allow the protuberance to snap into position within slot 16. As the protuberance snaps into the slot, both an audible sound will result and a tactile sensation will be experienced by the technician interconnecting the components. A further tactile signal is given to the technician by the previously described, second locking means of the invention which comprises circumferential extending protuberance 48. As the Y site connector is moved into locking engagement with the connector 12, the enlarged diameter head portion 64 of the Y site will engage the protuberance 48 and, upon the continued exertion of an inward mating force, will cause wall 14 to yieldably deform permitting the head portion to slide past the protuberance into the locking position shown in FIG. 7.

With the connector 12 and the Y site interconnected in the manner thus described and as shown in FIG. 6, the Y site unit will be securely and stably maintained in position within the connector without any appreciable wobbling or without any pistoning of the cannula within the septum 58. When it is desired to disconnect the components, an inward force exerted on gripping members 44 will cause elements 38 to separate a sufficient distance to permit passage thereby of upper portion 40a of protuberance 40 so that the Y site unit can be smoothly and easily disconnected form the connector 12.

Turning to FIG. 5, an alternate embodiment of the medical connector of the apparatus of the invention is there illustrated and generally designated by the numeral 66. This connector is similar in many respects to the previously described connector and like components are identified by like numerals. The primary difference between connector 66 and connector 12 resides in the fact that the plastic cannula has been replaced by a metal needle 68 which is securely held in position by an end wall 70 which closes the second end 72 of the cylindrically shaped sheath portion 74 of the connector. Sheath portion 74 is provided with a slot 16 and with locking elements 38 of the character previously described in connection with the connector 12. Similarly, connector 66 is provided with a circumferentially extending slot 34 which is disposed intermediate first and second portions 74a and 74b of shroud 74. Connector 66 is mated with the Y site unit of the character shown in FIG. 6 in the same manner as previously described with metal cannula or needle 68 penetrating septum 58 as the components are moved into locking engagement.

Turning now to FIGS. 8 through 12, another form of low dead space Y site unit of the present invention is there illustrated. This unit is similar in many respects to the Y site unit previously described and like numerals are used to identify like elements. The Y site unit of this embodiment of the invention comprises a tubular body portion 80 and an arm portion 82 which extends laterally therefrom. The Y site also includes first and second ports 84 and 86, port 84 being closed by a uniquely constructed penetrable seal 58 (see also FIG. 13). The Y site of this form of the invention also includes a locking protuberance 88 which includes an upper plate-like portion 88a which is connected to a stem-like portion 88b. Portion 88b is provided with a slit 99 and, in turn, interconnected with tubular body portion 80. Extending outwardly from body portion 80, on the opposite side of the body from protuberance 88, is a thinlike protuberance 90 which is adapted to engage the interior wall of sheath portion 14 of connector 12. This protuberance engages the interior wall of sheath portion 14 in a manner to assist in stabilizing the connection and to positively prevent any wobbling of the Y site relative to the medical connector when the two parts are mateably interconnected.

Figure 9:
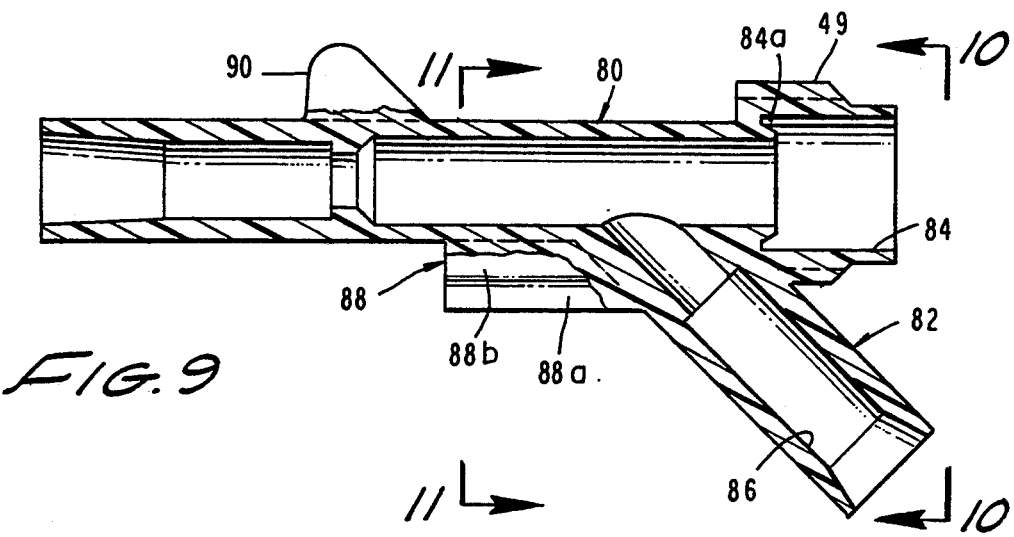
FIG. 9 is a cross-sectional view taken along lines 9—9 of FIG. 8.

A study of FIG. 9 shows that the opening 84 in the unit is specially constructed so as to accept the uniquely configured septum 58, the character of which is best seen in FIG. 13. More particularly, opening 84 is provided with a circumferentially extending groove 84a which accepts a circumferentially extending flange-like portion 58a provided on septum 58. Septum 58 also includes a reduced diameter portion 58b which is closely received within the central bore of body portion 80 of the Y site. With this construction, dead space within the Y site unit is virtually eliminated thereby preventing entrapment of fluids within the Y site in the manner which is common in commercially available Y sites of traditional design.

Figure 10:
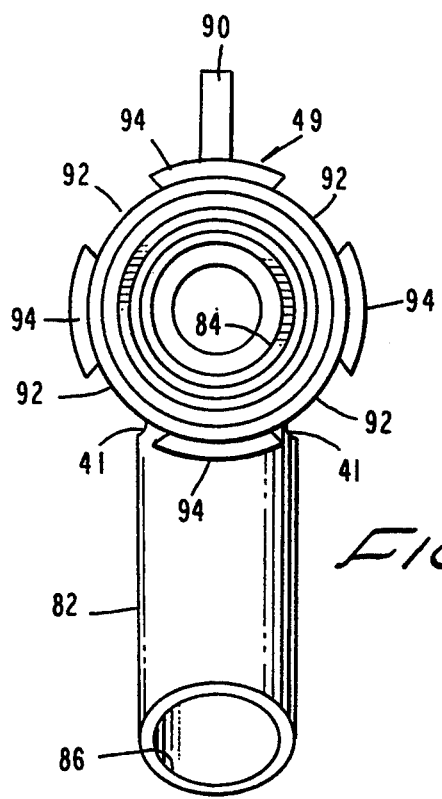
FIG. 10 is a view taken along lines 10—10 of FIG. 9.
Figure 11:
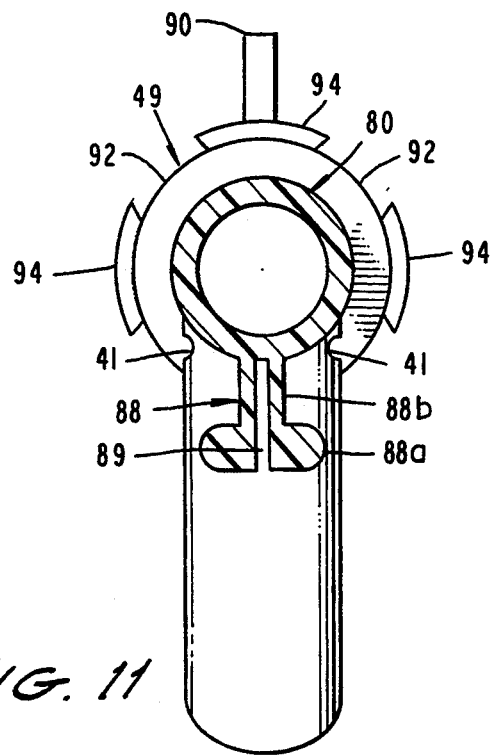
FIG. 11 is a cross-sectional view taken along lines 11—11 of FIG. 9.
Figure 25:
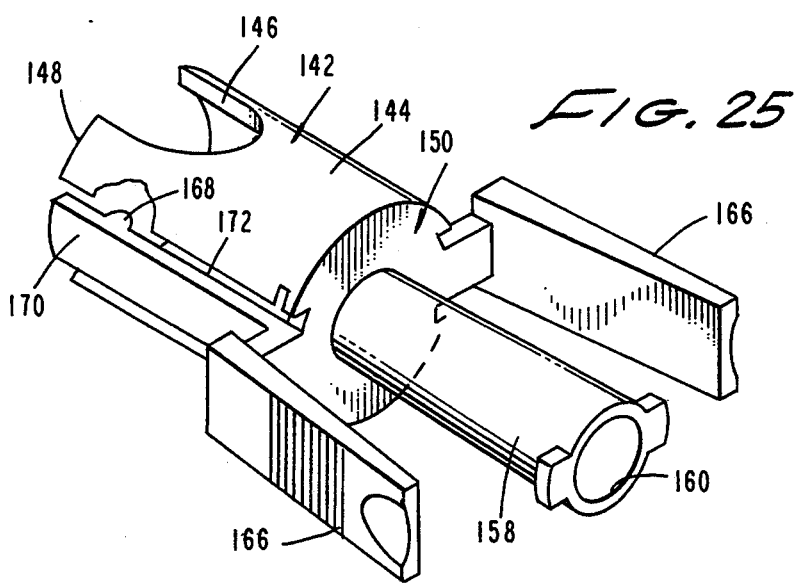
FIG. 25 is a generally perspective view of yet another form of connector of the apparatus of the present invention.

As best seen by referring to FIG. 10, head portion 49 of the Y site of this form of the invention is provided with a plurality of circumferentially spaced grooves 92 which cooperate to define a plurality of circumferentially spaced lands 94. Lands 94 function to engage the inner wall of shroud 14 of the connector in the manner indicated in FIG. 6 and thereby function to guide the connector over the Y site and further prevent wobbling of the connector relative to the Y site.

Turning particularly to FIGS. 13, 14 and 15, a highly novel feature of the embodiment of the Y site of the present invention resides in the fact that the septum 58 is provided with a uniquely configured slit 95. Septum 58 is preferably constructed from a resiliently deformable material such as soft rubber or synthetic rubber, or the like and is provided with the slit 95 by means a cutting tool 97 of the configuration illustrated in FIG. 15. More particularly, tool 97 and slit or cut 95 comprise a forwardly extending knife-like portion 97a which terminates at its forward end at a cutting point 97b. The opposite end of the tool 97 flares out to define oppositely disposed, angularly-outwardly extending arms 97c. When the tool 97 is inserted into the specimen, the cut 95 will be made and will conform to the shape of the tool 97 and provide the novel longitudinally extending radically inwardly tapering slip 95.

The opening 84 which accepts septum 58 is specially sized so as to uniquely control the compressive forces that seal the rubber body of the septum around the cannula. Compression of the rubber helps maintain leak-free contact with the entire circumference of the cannula and wipe the surface of the cannula clean, so that it does not introduce foreign matter into fluids for intravenous administration. With the construction thus described, when the blunt cannula 24 is inserted into the septum, the cut will expedite entry and withdrawal of the septum which at the same time causing a continuous, uniform, inward radial force to be exerted on the septum tending to positively seal against leakage around the cannula.

Turning to FIG. 16, an alternate form of septum 98 is there illustrated. Septum 98 is also constructed from a resiliently deformable material such as soft rubber and has the exterior configuration of septum 58. However, septum 98 is adapted for use with a metal cannula or needle of the character identified in FIG. 16 by the numeral 99. Septum 98 is provided with an inboard cavity 98a which functions to permit easier entry of cannula 99 into and through the septum 98. Cavity 98a is generally cylindrical in shape and extends inwardly from the inboard end of the septum 98, a distance of approximately one-third of the length of the septum 98. Because of the overall length of the septum 98, a sufficient needle engaging area remains to ensure sealable interconnection of the cannula 99 with the septum 98.

Turning now to FIGS. 17 through 24, another form of medical connector of the apparatus of the invention is there shown and generally designated by the numeral 102. The connector of this form of the invention is also adapted for use with a Y site of the character having a cylindrical body portion and an arm portion extending laterally therefrom. The connector comprises a generally cylindrical wall 104 having an elongated slot 106 for receiving the arm portion of the Y site unit (FIG. 21). Wall 104 includes an open first end 108 and a second end 110 which, as best seen in FIG. 20, is closed by an end wall 112. End wall 112 functions as a cannula support for supporting either a metal or plastic cannula.

The cannula shown in FIGS. 17 through 24 comprises a plastic cannula 114 which is connected to cannula support wall 112 and extends inwardly a substantial distance into the interior of sheath portion 104 in the manner best seen in FIG. 20. Cannula 114 comprises a tapered wall 116 one end of which interconnects with cannula support wall 112 in the manner shown in FIG. 20. As before, cannula wall 116 may be integrally formed with wall 112 or, in some instances, may comprise a separate element which is either fixedly or removably interconnected with wall 22.

Extending rearwardly of wall 112 is a connecting portion 118 having a fluid passageway 120 which communicates with a fluid passageway 122 defined by cannula wall 116. Portion 118 can be suitably interconnected with a source of liquid such as a parenteral fluid 60 by means of a luer connector, a length of plastic tubing or in any other suitable manner well known to those skilled in the art.

Forming an important aspect of the connector of this alternate form of the connector of the invention is another type of locking means for releasably locking a Y site, such as that shown in FIGS. 8 through 13, in position within the connector. These locking means also comprise first and second locking means. More particularly, the locking means include a novel first locking means of a character presently to be described and a second locking means provided in the form of a circumferentially extending bead 126 which is located on the inner circumference of wall 104 of the sheath assembly. As the head portion of the Y site enters the connector, it will frictionally engage bead 126. However, upon the continued exertion of an inward force on the Y site the head portion 49 (see also FIGS. 8 and 9) will slip by bead 126 giving a tactile sensation. The Y site will then move forwardly into the locking position shown in FIG. 20 where cannula 114 has penetrated the septum 58 of the Y site. It is to be noted that when the Y site is in the locking position, the cannula tip is uniquely located proximate the intersection of the axial fluid passageway of the Y site and the fluid passageway of the arm of the Y site.

The second locking means of this alternate form of connector of the invention comprises a locking ring 130 which is rotatably connected to sheath 104 proximate its open end 108. Ring 130 is disposed within the cylindrical boundary of the sheath assembly and is provided with a slot 132 as well as circumferentially spaced, inwardly extending ribs 134 which are receivable within grooves 136 formed in sheath 104 (FIG. 18). With this construction ring 130 can be rotated from the first unlocked configuration shown in FIG. 21 wherein slot 132 is indexed with slot 106 formed in wall 104 to the second locked configuration shown in FIG. 23. To facilitate rotation of ring 130, longitudinally extending striations 135 are provided on the exterior surface of the ring.

As best seen in FIGS. 17 and 20, wall 104 includes an outwardly tapering portion 104a which is provided with a circumferentially extending groove 104b. Groove 104b closely receives a tongue 130a provided on ring 130 and functions to guide smooth rotation of the ring relative to the sheath. Tongue 130a prevents undesirable, diametrical deformation of the open end of wall 104 while tapering portion 104a provides a smooth transition between the cylindrical wall and the ring so as to prevent snagging of the connector assembly on tubing, clothing or other articles.

In using the apparatus of this latest form of the invention, ring 130 is rotated to the position shown in FIG. 21. In this position, slot 106 in wall 104 is indexed with the slot 132 provided in ring 130 so that the Y site unit can be readily inserted into the interior of the sheath with the arm portion 52 of the Y site being freely movable within slots 106 and 132. It is to be noted that slot 132 in ring 135 has rounded edges so as to facilitate entry of the arm portion 52 of the Y site unit. As the Y site unit is moved inwardly of the ring and cylindrical wall 104, the head portion of the Y site will engage circumferential protuberance 126 and will create a first locking which is tactilely observable by the operator. At the same time that the Y site unit is urged into the connector assembly, cannula 116 will pierce the slit septum 58 in the manner previously described.

Once the Y site is in the position shown in FIG. 20, ring 135 can be rotated from the unlocked position shown in FIG. 21 into the locked position shown in FIG. 23. In this position, the arm portion 52 of the Y site blocks retraction of the Y site from the connector assembly.

An important feature of the locking means of this latest form of the invention resides in the configuration of the mating protuberances 134 provided on ring 130 and the interrupted groove 136 provided on sheath 104. More particularly, it is to be noted that protuberances 134 are spaced apart and are provided with tapered edges 134a which will ride over interruptions 136a provided in groove 136 (FIG. 18). With this construction as the ring 130 moves into a locking position with respect to sheath 104, the operator will experience a tactile sensation of locking as interruptions 136a come to rest intermediate protuberances 134a. In this way, the operator is assured that the ring has moved into the desired locking position preventing withdrawal of the Y site unit from the connector. Protuberances 134 when received within groove 136 prevent accidental separation of the ring from the sheath body.

For certain applications, ring 130 may also be constructed of a plastic material having a color different from the plastic material used in the construction of the sheath body. With this arrangement, when the ring is in a locking position, the fact that the slot 106 is covered by the ring is readily observable at a considerable distance from the patient.

When it is desired to remove the Y site from the connector unit, ring 130 is, of course, rotated once again to the unlocked position shown in FIG. 21. A withdrawal force exerted on the Y site will then cause the head of the Y site to pass over protuberance 126 and will permit the arm 52 of the Y site to freely pass through the indexed slots 106 and 132.

Referring to FIGS. 25 through 31, another form of medical connector of the apparatus of the invention is there shown and generally designated by the numeral 142. The connector of this form of the invention is also adapted for use with a Y site of the character having a cylindrical body portion and an arm portion extending laterally therefrom. The connector comprises a generally cylindrical wall or skirt 144 having an elongated slot 146 for receiving the arm portion of the Y site unit (FIG. 30). Cylindrical wall 144 protects the septum from contamination and is preferably constructed from a thin plastic and includes an open first end 148 and a second end 150 which, as best seen in FIG. 30, is closed by an end wall 152. End wall 152 functions as a cannula support for supporting either a metal or plastic cannula.

Figure 26:
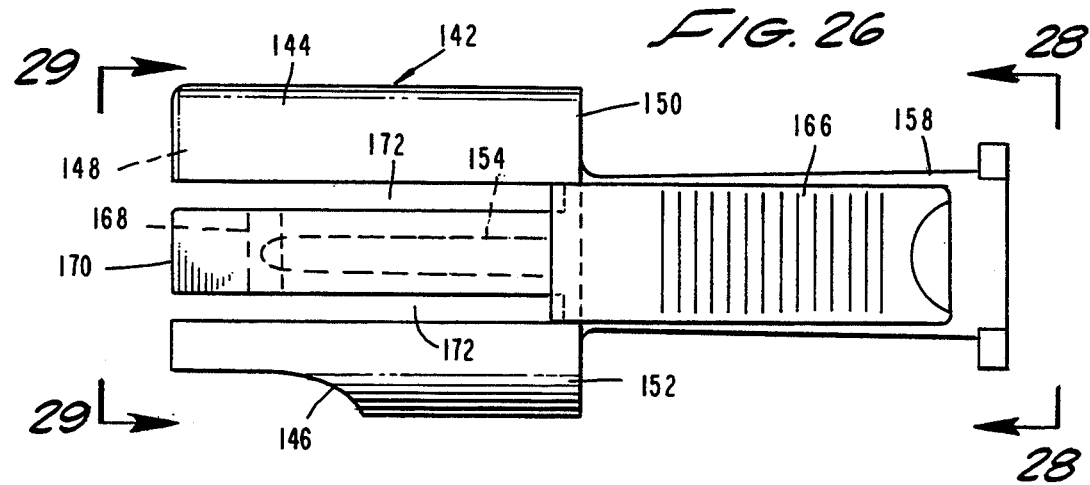
FIG. 26 is a side elevational view of the connector shown in FIG. 25.
Figure 27:
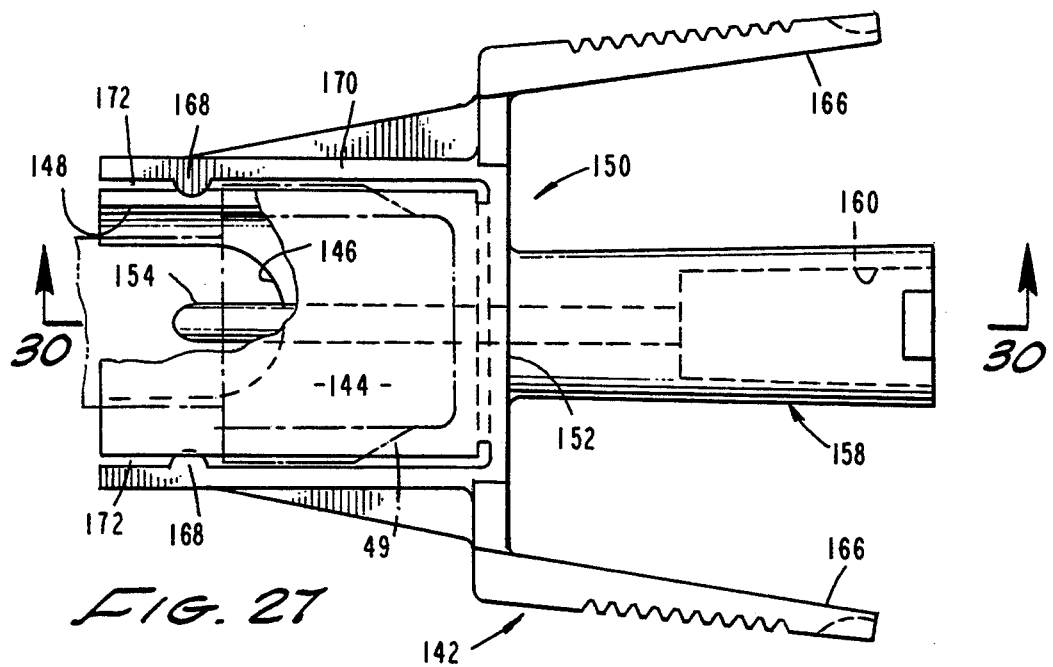
FIG. 27 is a bottom view of the connector and showing, in fragmentary form, a Y site interconnected with the connector, the drawing being partly broken away to show internal construction.

The cannula shown in FIGS. 27 through 31 comprises metal cannula or needle 154 which is connected to end wall 152 and extends inwardly a substantial distance into the interior of sheath portion 144 in the manner best seen in FIG. 26.

Extending rearwardly of wall 152 is a connecting portion 158 having a fluid passageway 160 which communicates with a fluid passageway 162 provided in needle 154. Portion 158 can be suitably interconnected with a source of liquid such as a parenteral fluid by means of a luer connector, a length of plastic tubing or in any other suitable manner well known to those skilled in the art. As best seen in FIG. 30, portion 158 has a solid section 158a which assists in rigidly supporting needle 154.

Forming an important aspect of the connector of this latest form of the connector of the invention is locking and release means for releasably locking a Y site of the character shown in FIGS. 30 and 31 in position within the connector. These locking and release means here comprise a clothes-pin like locking mechanism which includes a pair of actuating arms 166 connected to sheath portion 144 and extending rearwardly from wall 152 in a direction toward connector portion 158. The locking means here includes a circumferentially extending bead 168 which is provided on the inner wall of each of a pair of oppositely-disposed, resiliently-deformable locking members 170 which comprise the locking means of the connector. Locking members 170 are defined by circumferentially-spaced, longitudinally-extending slits 172 (FIG. 126) provided in cylindrical wall 144 of the sheath assembly. Once again locking members 170 are contained within a cylindrically shaped boundary of the character previously defined.

In using the apparatus of this form of the invention, as the head portion of the Y site enters the connector, it will frictionally engage bead 168. However, upon the continued exertion of an inward force on the Y site, locking arms 170 will spring outwardly in the manner shown in FIG. 31 permitting the head portion 49 to slip by beads 168 and to move forwardly into the locking position shown in FIG. 31 where cannula 154 has penetrated the septum 58 of the Y site. In the locked position, the Y site arm is received within slot 146 and protuberances 94 prevent the Y site from wobbling within the connector.

Once the Y site is in the locked position, it can be removed from the connector only by operation of the release means, that is by squeezing arms 166 inwardly in the direction of the arrow 167 in FIG. 31. This force causes one or both of the locking arms to resiliently move outwardly in the direction of the arrow 169 so that the head portion of the Y site will clear beads 168 permitting easy retraction of the Y site from the connector.

Turning now to FIGS. 32, 33 and 34, the use of the previously described medical connector 66 with a low dead space heparin lock of the present invention is there illustrated. As best seen in FIG. 32, one form of the low dead space heparin lock of the invention comprises a tubular body portion 180 having an enlarged diameter head portion 182. The heparin lock also includes first and second ports 184 and 186, the first port 184 being closed by a uniquely constructed penetrable seal 58 of the character previously described. An important feature of the heparin lock of this form of the invention, is the locking protuberance 188 which functions to lockably engage barb-like segments 38 provided on the cylindrical wall of the sheath of the connector unit. The configuration of protuberance 188 is best seen by referring to FIG. 34 where it is to be noted that the protuberance includes a plate-like portion 188a which is connected to a body portion 188b which, in turn, is interconnected with tubular body portion 50. In addition to performing the locking function, protuberance 188 uniquely functions as an anti-roll means for preventing the heparin lock from rolling on a flat surface such as a table top and the like.

The heparin lock of the invention also includes an enlarged diameter portion 190 disposed at the opposite end of the tubular body portion 180 from head 182. Portion 190 surrounds the inwardly tapering end portion 180a of portion 180 and includes a plurality of circumferentially extending beads 180b (FIG. 33). Lockably receivable within portion 190 is a connector member 192 of standard construction.

In using the apparatus of the invention, the medical connector 66 is interconnected with a suitable source of liquid to be infused in the patient such as a parenteral liquid contained within a suitable source such as a bottle or elevated flexible bag. The heparin lock is then inserted into the open mouth of cylindrical wall 14 and urged inwardly with sufficient force to cause cannula 68 to penetrate septum 58. As the heparin lock is introduced into the connector unit, protuberance 188 of the device will ride along curved surfaces 38b of the shroud urging them to separate. Because the shroud is provided with the previously identified, strategically located, circumferentially extending slot 34, the locking elements 38 will be permitted to resiliently deform outwardly a sufficient distance to allow the protuberance to snap into position within slot 16. As the protuberance snaps into the slot, both an audible sound will result and a tactile sensation will be experienced by the technician interconnecting the components. A further tactile signal is given to the technician by the previously described, second locking means of the invention which comprises circumferential extending protuberance. As the heparin lock is moved into locking engagement with the connector 66, the enlarged diameter head portion 182 will engage the protuberance 48 and, upon the continued exertion of an inward mating force, will slide past the protuberance into the locking position shown in FIG. 33.

With the connector 12 and the heparin lock interconnected in the manner thus described, the heparin lock will be securely and stably maintained in position within the connector without any appreciable wobbling or without any pistoning of the cannula within the septum 58. When it is desired to disconnect the components, an inward force exerted on gripping members 44 will cause elements 38 to separate a sufficient distance to permit passage thereby of upper portion 188a of protuberance 188 so that the heparin lock can be smoothly and easily disconnected form the connector 66.

Turning to FIGS. 48, 49 and 50, another form of low dead space heparin lock of the present invention is there illustrated. This form of the heparin lock comprises a tubular body portion 195 having an octagonal head portion 195a. The heparin lock includes first and second ports one of which is closed by a penetrable seal 58 of the character previously described. An important feature of this second form of heparin lock is the differently configured locking protuberance 197 which functions to lockably engage barb-like segments 38 provided on the cylindrical wall of the sheath of the connector unit. The configuration of protuberance 197 is best seen by referring to FIG. 49 where it is to be noted that the protuberance includes a generally triangularly shaped, plate-like portion 197a which is connected to a body portion 195.

In using the apparatus of the invention, the medical connector 66 is interconnected with a suitable source of liquid to be infused in the patient such as a parenteral liquid contained within a suitable source such as a bottle or elevated flexible bag. The second form of heparin lock is then inserted into the mouth of cylindrical wall 14 and urged inwardly with sufficient force to cause cannula 68 to penetrate the septum. As the heparin lock is introduced into the connector unit, protuberance 197 of the device will ride along curved surfaces 38b of the shroud urging them to separate and deform in the same manner as previously described. As before, exertion of an inward mating force will cause protuberance 197 to slide past the curved surfaces and lock in place providing both an audio and a tactile signal.

Figure 35:
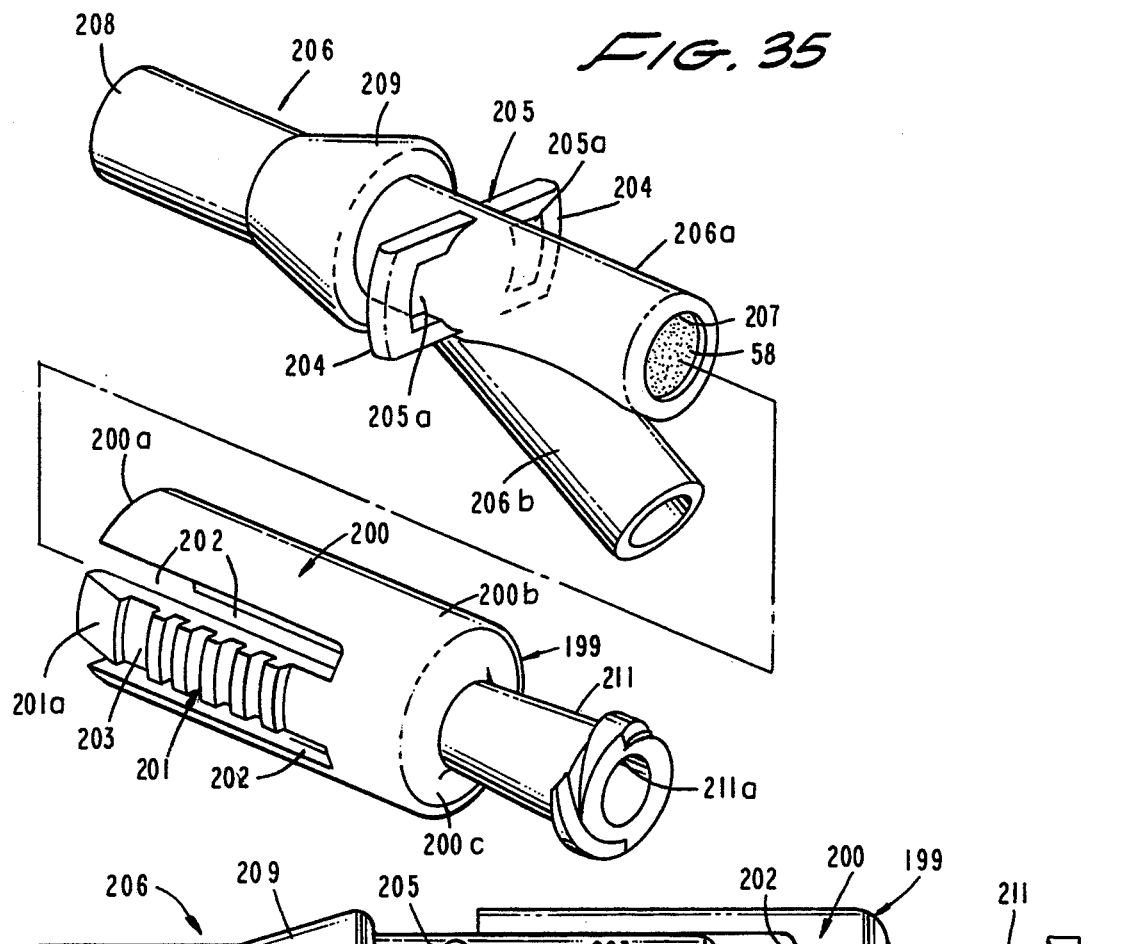
FIG. 35 is a generally perspective, exploded view of an alternate form of Y site unit and a connector therefor.
Figure 36:
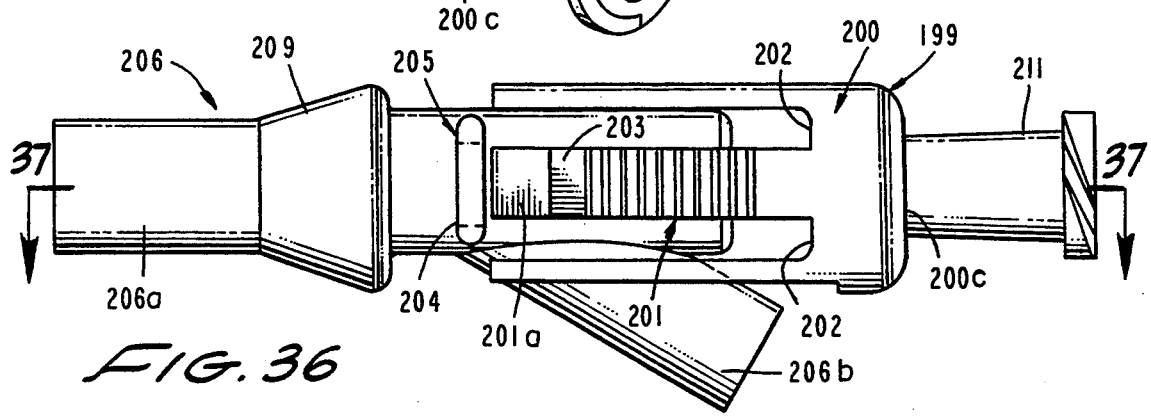
FIG. 36 is a side elevational view of the Y site of FIG. 35 partially interconnected with the connector of FIG. 35.
Figure 37:
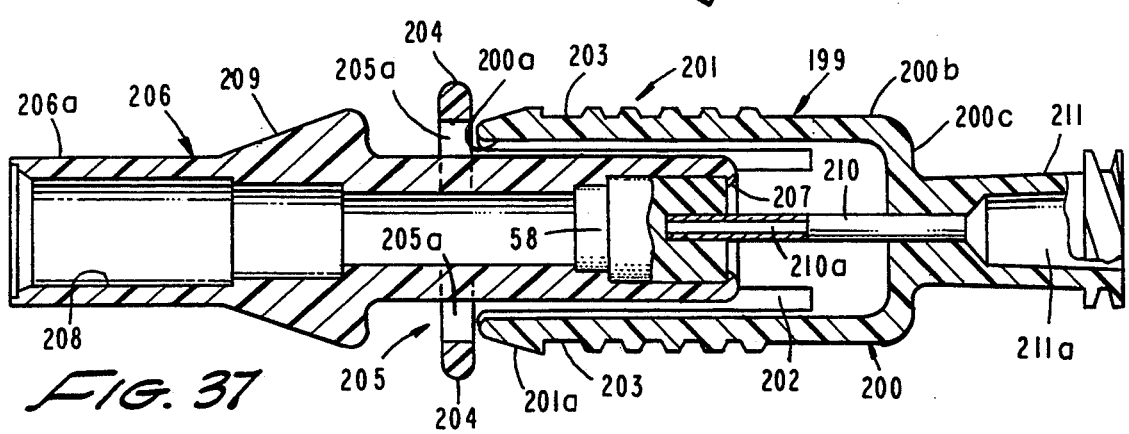
FIG. 37 is a cross-sectional view taken along lines 37—37 of FIG. 36.

Referring to FIGS. 35 through 37, still another embodiment of a Y site and medical connector combination of the apparatus of the invention is there illustrated. This connector 199 is similar in many respects to the previously described connector and includes a generally cylindrical wall 200 having a pair of oppositely disposed, resiliently deformable locking members 201 defined by longitudinally extending slits 202 (FIG. 35). Each locking member has a tapered extremity 201a and is provided with a locking groove 203 which is adapted to lockably receive the outer end portions 204 of a lock means shown here as a locking collar 205 provided on the Y site unit which is generally designated in the drawings by the numeral 206. Locking members 201 and the lock means or locking collar 205, which comprise the principal components of the locking means of this form of the invention are substantially contained within the cylindrical boundary of the sheath assembly.

The low dead space Y site unit 206 of this embodiment is similar in many respects to the Y site unit previously described and includes a tubular body portion 206a and an arm portion 206b which extends laterally therefrom. The Y site also includes first and second ports 207 and 208, port 207 being closed by a uniquely constructed penetrable seal 58 (see also FIG. 13). The Y site of this form of the invention includes, in addition to locking collar 205, an enlarged diameter frustoconically shaped portion 209 which functions as a stop for connector 199.

As best seen in FIG. 37, sheath portion 200 includes an open first end 200a and a second end 200b which is closed by an end wall 200c. End wall 200c functions as a cannula support for supporting either a metal or plastic cannula. The cannula 210 shown in FIG. 37 is connected to cannula support wall 200a and extends inwardly a substantial distance into the interior of sheath or wall portion 200.

Extending rearwardly of wall 200c is a connecting portion 211 having a fluid passageway 211a which communicates with a fluid passageway 210a defined by the cannula wall. Portion 211 can be suitable interconnected with a source of liquid such as a parenteral fluid by means of a luer connector, a length of plastic tubing or in any other suitable manner well known to those skilled in the art.

In using the apparatus of this latest form of the invention, the connector is rotated to the position shown in FIGS. 36 and 37. In this position, members 201 of the sheath portion are indexed with slots 205a provided in collar 205. In this position, the Y site unit can be readily inserted into the interior of the sheath with the arm portion 206b of the Y site being receivable within the arm receiving slot of the connector. As the Y site unit is moved inwardly of the sheath, the cannula will pierce the slit septum 58 in the manner previously described in connection with the earlier described embodiments of the Y site unit. Continued movement of the Y site moves into the position shown in FIG. 37, will cause members 201 to be urged inwardly into slots or openings 205a and portions 204 will snap into grooves 203. In this position, the locking members 201 prevent retraction of the Y site from the connector assembly. To remove the Y-site an inward squeezing pressure is exerted proximate the mid-points of members 201. This inward pressure permits end portions 201 to slip under portions 204 of the collar 205.

Figure 38:
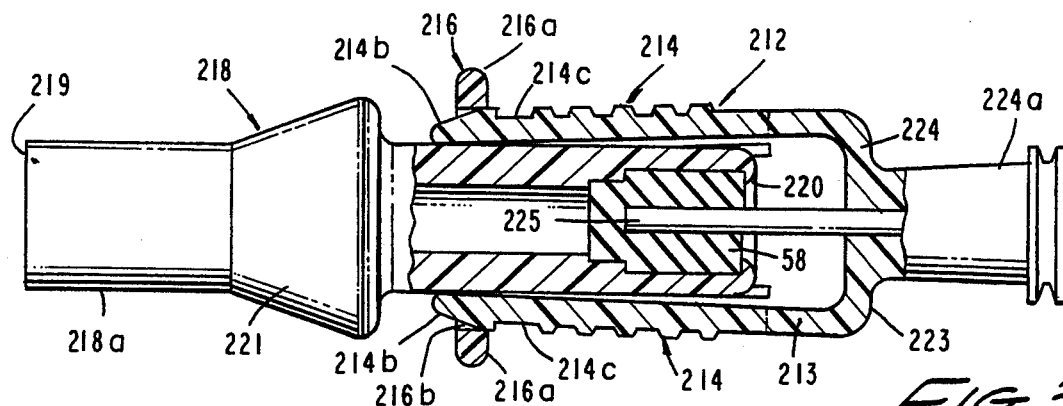
FIG. 38 is a cross-sectional view similar to FIG. 37 but showing the components moving toward a locked position.
Figure 39:
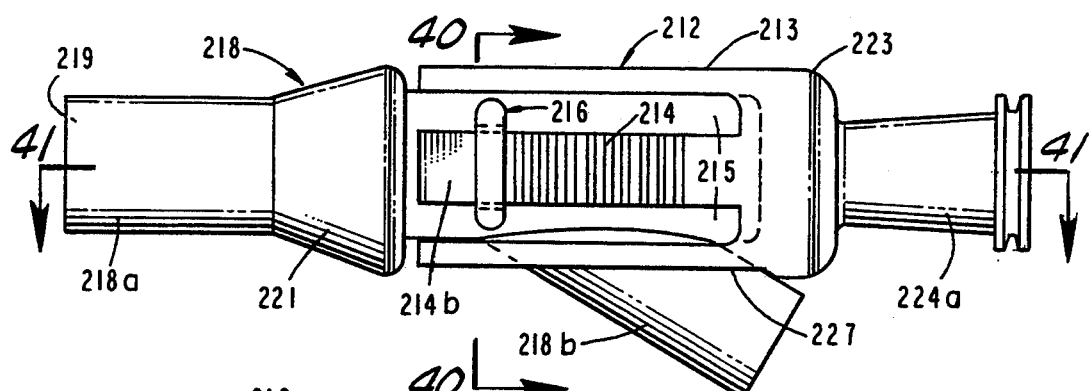
FIG. 39 is a side elevational view of the Y site unit of this form of the invention interconnected with the connector unit of this form of the invention.

Turning to FIGS. 38 through 41, still another embodiment of a Y site and medical connector combination of the apparatus of the invention is there illustrated. This connector 212 is similar in many respects to the previously described connector and includes a generally cylindrical wall 213 having a pair of oppositely disposed, resiliently deformable locking members 214 defined by longitudinally extending slits 215 (FIG. 39). Each locking member has a tapered extremity 214b and is provided with a locking groove 214c which is adapted to lockably receive the outer end portions 216a of a lock means shown here as a locking collar 216 provided on the Y site unit which is generally designated in the drawings by the numeral 218. Locking members 214 and locking collar 202, which comprise the principal components of the locking means of this form of the invention are substantially contained within the cylindrical boundary of the sheath assembly.

The low dead space Y site unit 218 of this embodiment is similar in many respects to the Y site unit previously described and includes a tubular body portion 218a and an arm portion 218b which extends laterally therefrom. The Y site also includes first and second ports 219 and 220, port 220 being closed by a uniquely constructed penetrable seal 58 (see also FIG. 13). The Y site of this form of the invention includes, in addition to the ring like locking collar 216, an enlarged diameter frustoconically shaped portion 221 which functions as a stop for connector 193.

Figure 41:
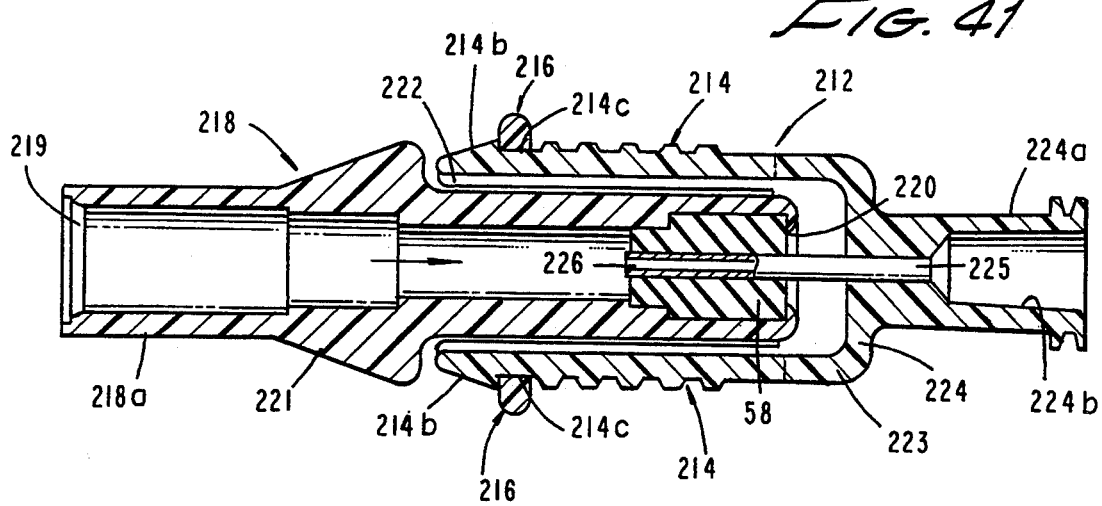
FIG 41 is a cross-sectional view taken along lines 41—41 of FIG. 39.

As best seen in FIG. 41, sheath portion 213 includes an open first end 222 and a second end 223 which is closed by an end wall 224. End wall 224 functions as a cannula support for supporting either a metal or plastic cannula. The cannula 225 shown in FIGS. 38 and 41 is connected to cannula support wall 224 and extends inwardly a substantial distance into the interior of sheath portion 213.

Extending rearwardly of wall 224 is a connecting portion 224a having a fluid passageway 224b which communicates with a fluid passageway 226 defined by the cannula wall. Portion 224a can be suitably interconnected with a source of liquid such as a parenteral fluid by means of a luer connector, a length of plastic tubing or in any other suitable manner well known to those skilled in the art.

Figure 40:
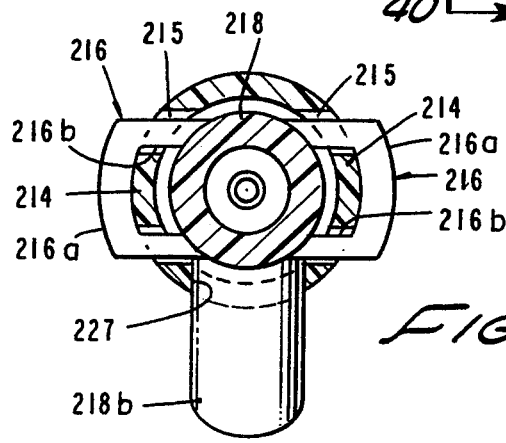
FIG. 40 is a cross-sectional view taken along lines 40—40 of FIG. 39.

In using the apparatus of this latest form of the invention, the connector is rotated to the position shown in FIGS. 38 and 39. In this position, the Y site arm receiving slot 227 is aligned with the Y site arm and members 214 of the sheath portion are indexed with the slots 216b provided in collar 216 (FIG. 40). In this position, the Y site unit can be readily inserted into the interior of the sheath with the arm portion 218b of the Y site being receivable within the arm receiving slot of the connector. As the Y site unit is moved inwardly of the sheath, the cannula will pierce the slit septum 58 in the manner previously described in connection with the earlier described embodiments of the Y site unit. Continued movement of the Y site moves into the position shown in FIG. 38, will cause members 214 to be urged inwardly into slots or openings 216b and portions 216a will snap into grooves 214c. In this position, the locking members 214 prevent retraction of the Y site from the connector assembly.

Figure 42:
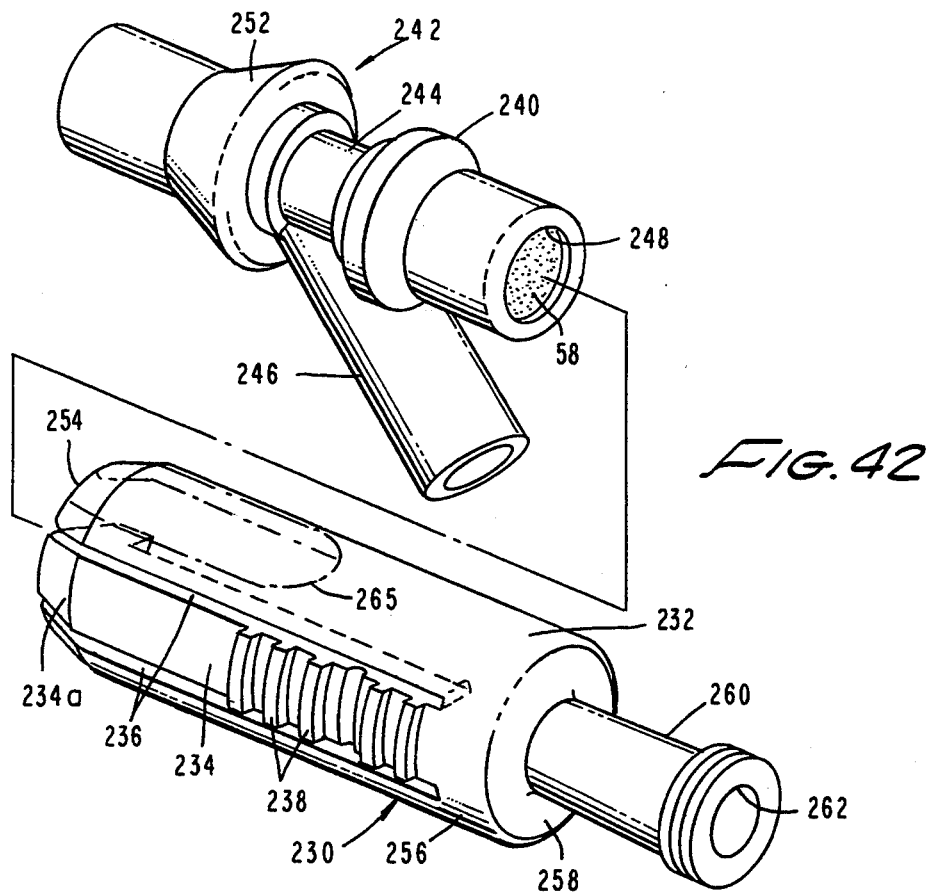
FIG. 42 is a generally perspective, exploded view of yet another form of Y site unit and connector of the apparatus of the invention.
Figure 43:
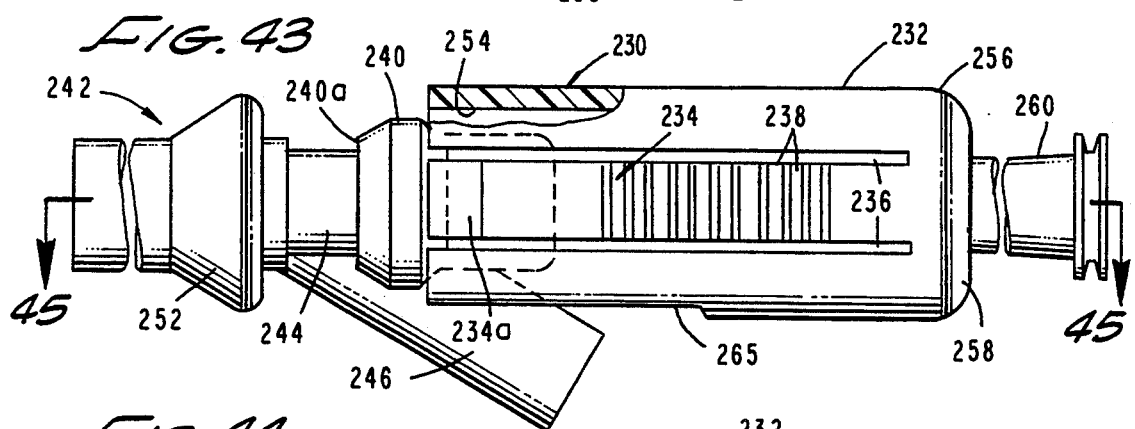
FIG. 43 is a side elevational view partly in section of the Y site unit and connector of FIG. 42 shown in a partially connected configuration.

Referring next to FIGS. 42 through 47, yet another embodiment of a Y site and medical connector combination of the apparatus of the invention is there illustrated. The connector shown in FIG. 42, which is currently designated by the numeral 230, is similar in many respects to the previously described connector 193 and includes a generally cylindrical wall 232 having a pair of oppositely disposed, resiliently deformable locking members 234 defined by longitudinally extending slits 236 (FIG. 43). Each locking member has a hook-like extremity 234a and is provided with longitudinally spaced grooves 238. Locking member 234 and an enlarged diameter locking protuberance 240 formed on the Y site unit are substantially contained within the cylindrical boundary of the shroud assembly and comprise the principal components of the locking means of this form of the invention.

As best seen in FIG. 42, the low dead space Y site unit 242 of this embodiment of the invention is similar in many respects to the Y site unit previously described and includes a tubular body portion 244 and an arm portion 246 which extends laterally therefrom. The Y site also includes first and second ports 248 and 250, port 248 being closed by a uniquely constructed penetrable seal 58 (see also FIG. 13). The Y site of this form of the invention includes, in addition to the locking protuberance 240, an enlarged diameter frustoconically shaped portion 252 which functions as a stop for connector 230.

As best seen in FIG. 46, sheath portion 232 includes an open first end 254 and a second end 256 which is closed by an end wall 258. End wall 258 functions as a cannula support for supporting either a metal or plastic cannula.

The cannula 260 shown in FIGS. 45 and 46 is connected to cannula support wall 258 and extends inwardly a substantial distance into the interior of sheath portion 232.

Extending rearwardly of wall 258 is a connecting portion 260 having a fluid passageway 262 which communicates with a fluid passageway 264 defined by the cannula wall. Portion 264 can be suitably interconnected with a source of liquid such as a parenteral fluid by means of a luer connector, a length of plastic tubing or in any other suitable manner well known to those skilled in the art.

Figure 44:
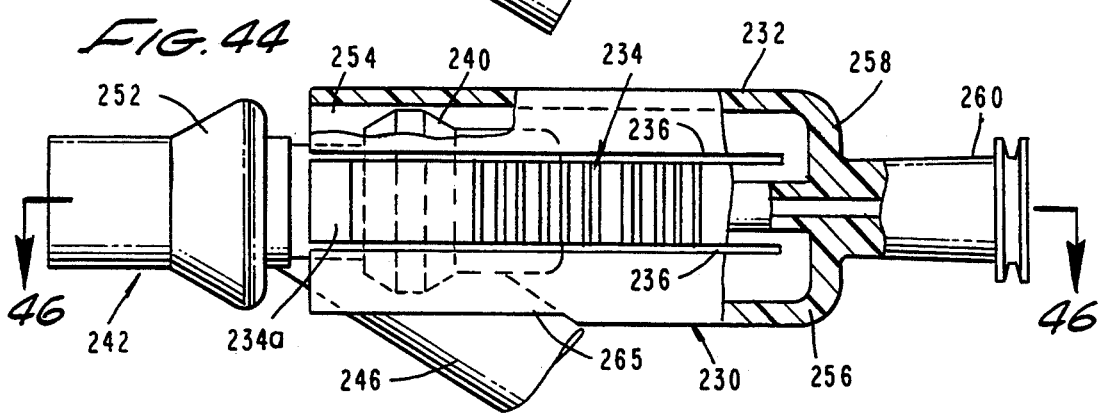
FIG. 44 is a view similar to FIG. 43 but showing the component parts fully interconnected.

In using the apparatus of this latest form of the invention, the connector is rotated to the position shown in FIGS. 43 and 44. In this position, arm receiving slot 265 of the sheath portion is aligned with arm 246 of the Y site. In this position, the Y site unit can be readily inserted into the interior of the sheath with the arm portion of the Y site being receivable within the arm receiving slot of the connector. As the Y site unit is moved inwardly of the sheath, the cannula will pierce the slitted septum 58 in the manner previously described in connection with the earlier described embodiments of the Y site unit.

As the Y site moves into the position shown in FIG. 47, members 234 will be urged outwardly in the manner shown by the phantom lines and ends 234a will slide over protuberance 240 and will snap with an accompanying audio signal into locking engagement with shoulders 240a provided in protuberance 240. In this position, shoulders 240a prevent disengagement of the connector from the Y site unit

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for infusing liquids into a patient comprising:
   (a) a Y site having a tubular body portion and an arm portion extending laterally therefrom, said tubular portion having a locking member and first and second ports, said first port being closed by a penetrable seal; and
   (b) a connector for releasable interconnection with said Y site, said connector comprising:
      (i) a cannula; and
      (ii) a sheath assembly including a body having a longitudinally extending central axis and comprising a cylindrical wall surrounding said cannula over its length, said wall having a slot for receiving said arm portion of said Y site and including first locking means for locking engagement with said locking member of said Y site to lockably interconnect said connector with said Y site, said locking means being movable from a first locked position to a second unlocked position and comprising a pair of longitudinally extending locking members defined by spaced apart longitudinally extending slits provided in said cylindrical wall of said body, said locking members being yieldably deformable from a first position substantially parallel with said central axis to a second, non-parallel position.

2. An apparatus for infusing liquids into a patient comprising:
   (a) a Y site having a tubular body portion and an arm portion extending laterally therefrom, said tubular portion having a locking member and first and second ports, said first port being closed by a penetrable seal, said locking member comprising a locking protuberance extending radially outwardly from said body portion and including a stem portion and an enlarged plate-like portion; and
   (b) a connector for releasable interconnection with said Y site, said connector comprising:
      (i) a cannula; and
      (ii) a sheath assembly including a body comprising a cylindrical wall surrounding said cannula over its length, said wall having a slot for receiving said arm portion of said Y site and including first locking means for locking engagement with said locking protuberance of said Y site to lockably interconnect said connector with said Y site, said locking means being movable from a first locked position to a second unlocked position and being receivable between said tubular body portion of said Y site and said plate-like portion.

3. An apparatus as defined in claim 2 in which said connector provides an audible sound upon interconnection with said Y site.

4. An apparatus ad defined in claim 2 in which said connector provides a tactile sensation upon interconnection with said Y site.

5. A connector for releasable interconnection with an entry port structure having a body portion and first and second ports, said first port being closed by a penetrable seal, said connector comprising:
   (a) a generally cylindrical sheath portion for receiving the body portion of the entry port structure and having first and second ends, said first end being open to receive a portion of said entry port structure and a second end having cannula support and including first and second locking means for lockably engaging said entry port structure, said first locking means comprising a pair of longitudinally extending locking members defined by spaced-apart longitudinally extending slits formed in said sheath portion;
   (b) a cannula connected to said cannula support and extending into said sheath portion;
   (c) release means connected to said sheath portion for releasing said locking means to permit disconnecting of said sheath portion from said entry port structure.

6. A connector as defined in claim 5 in which said second locking means comprises a circumferential bead provided on said cylindrical sheath portion.

7. An apparatus for infusing liquids from a liquid source into a patient comprising:
   (a) a Y site having a tubular body portion and an arm portion extending laterally therefrom, said tubular portion having a locking member and first and second ports, said first port being closed by a penetrable seal, said locking member comprising a locking protuberance extending radially outwardly from said body portion and including side portions, a top portion and an end wall; and
   (b) a connector for releasable interconnection with said Y site, said connector comprising:
      (i) a cannula in communication with the liquid source; and
      (ii) a sheath assembly including a body comprising a cylindrical wall surrounding said cannula over its length, said wall having a slot for receiving said arm portion of said Y site and including first locking means for locking engagement with said locking protuberance of said Y site to lockably interconnect said connector with said Y site, said locking means being movable from a first locked position to a second unlocked position and being receivable between said tubular body portion of said Y site and said top portion of said protuberance.

8. An apparatus as defined in claim 7 in which said first locking means comprises a pair of spaced-apart, oppositely disposed locking ears, said locking ears being movable between first and second positions.

9. An apparatus as defined in claim 7 in which said connector further includes release means for releasing said locking means, said release means comprising spaced-apart gripping members extending from said sheath assembly.

10. An apparatus as defined in claim 7 in which said cylindrical wall of said body is provided with a circumferentially extending slot and in which said apparatus further includes release means for releasing said locking means to prevent disconnection of said connector with said Y site, said release means comprising a pair of spaced-apart gripping members extending tangentially from said wall of said body.

11. An apparatus as defined in claim 7 in which said connector provides an audible sound upon interconnection with said Y site.

12. An apparatus as defined in claim 7 in which said connector provides a tactile sensation upon interconnection with said Y site.

13. An apparatus as defined in claim 7 in which said puncturable seal comprises a septum having a cylindrical body constructed from a resiliently deformable material said body having an inwardly tapering slit.

14. A connector for releasable interconnection with an entry port structure having a body portion, including a locking protuberance extending therefrom and first and second ports, said first port being closed by a penetrable seal, said connector comprising:

(a) a generally cylindrical sheath portion for receiving the body portion of the entry port structure and having first and second ends, said first end being open to receive a portion of said entry port structure and a second end having cannula support and including locking means for lockably engaging the locking protuberance of the entry port structure, said locking means comprising a pair of spaced-apart, oppositely disposed locking ears movable from a first position in locking engagement with the locking protuberance to a second disengagement position;

(b) a cannula connected to said cannula support and extending into said sheath portion; and (c) release means connected to said sheath portion for releasing said locking means to permit disconnecting of said sheath portion from said entry port structure, said release means comprising a pair of spaced-apart gripping members extending tangentially from said sheath portion.

15. A connector as defined in claim 14 in which said connector provides both an audible sound and a tactile sensation upon interconnection with the entry port structure.

16. A connector as defined in claim 14 in which said sheath portion includes first and second wall portions and is provided with a circumferentially extending slot disposed intermediate said first and second wall portions.

17. A connector as defined in claim 16 in which said locking means further comprises a circumferential bead provided on said cylindrical wall of said body of said sheath assembly.

18. An apparatus as defined in claim 16 in which the locking protuberance of the entry port structure includes an end wall and in which said locking ears engage the end wall when said locking ears are in said first position.

* * * * *